(12) United States Patent
Beeckler et al.

(10) Patent No.: US 10,660,700 B2
(45) Date of Patent: May 26, 2020

(54) IRRIGATED BALLOON CATHETER WITH FLEXIBLE CIRCUIT ELECTRODE ASSEMBLY

(71) Applicant: BIOSENSE WEBSTER (ISRAEL) LTD., Yokneam (IL)

(72) Inventors: Christopher Thomas Beeckler, Brea, CA (US); Joseph Thomas Keyes, Glendora, CA (US); Assaf Govari, Yokneam (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 15/360,966

(22) Filed: Nov. 23, 2016

(65) Prior Publication Data

US 2017/0312022 A1     Nov. 2, 2017

Related U.S. Application Data

(63) Continuation-in-part of application No. 15/172,118, filed on Jun. 2, 2016, now abandoned, and a
(Continued)

(51) Int. Cl.
*A61B 18/14*     (2006.01)
*A61B 5/042*     (2006.01)
(Continued)

(52) U.S. Cl.
CPC .......... *A61B 18/1492* (2013.01); *A61B 5/042* (2013.01); *A61B 5/6853* (2013.01);
(Continued)

(58) Field of Classification Search
CPC ................................................ A61B 18/1492
See application file for complete search history.

(56) References Cited

U.S. PATENT DOCUMENTS

| 3,316,896 A | 5/1967 | Thomasset |
| 4,587,975 A | 5/1986 | Salo et al. |

(Continued)

FOREIGN PATENT DOCUMENTS

| CN | 102271607 A | 12/2011 |
| CN | 203539434 U | 4/2014 |

(Continued)

OTHER PUBLICATIONS

Copending U.S. Appl. No. 14/578,807, filed Dec. 12, 2014, 14 pages.
(Continued)

*Primary Examiner* — Daniel McNally
(74) *Attorney, Agent, or Firm* — Etan S. Chatlynne; Roberts Calderon Safran & Cole P.C.

(57) ABSTRACT

An irrigated balloon catheter for use in an ostium of a pulmonary vein, includes a flex circuit electrode assembly adapted for circumferential contact with the ostium when the balloon is inflated. Adapted for both diagnostic and therapeutic applications and procedures, the balloon catheter may be used with a lasso catheter or focal catheter. The flex circuit electrode assembly includes a substrate, a contact electrode on an outer surface of the substrate, the contact electrode having a "fishbone" configuration with a longitudinally elongated portion and a plurality of transversal fingers, and a wiring electrode on an inner surface of the substrate, and conductive vias extending through the substrate electrically coupling the contact electrode and the writing electrodes. Microelectrodes with exclusion zones are strategically positioned relative to the electrodes. The electrodes may also be split into electrode portions.

18 Claims, 18 Drawing Sheets

Related U.S. Application Data continuation-in-part of application No. 15/141,751, filed on Apr. 28, 2016.

(51) Int. Cl.

| | |
|---|---|
| *A61B 5/00* | (2006.01) |
| *G03F 7/16* | (2006.01) |
| *H05K 3/40* | (2006.01) |
| *H05K 3/46* | (2006.01) |
| *A61B 17/00* | (2006.01) |
| *A61B 18/00* | (2006.01) |

(52) U.S. Cl.
CPC .............. *A61B 5/6857* (2013.01); *G03F 7/16* (2013.01); *H05K 3/4038* (2013.01); *H05K 3/4644* (2013.01); *A61B 2017/00526* (2013.01); *A61B 2018/0016* (2013.01); *A61B 2018/0022* (2013.01); *A61B 2018/00029* (2013.01); *A61B 2018/00083* (2013.01); *A61B 2018/00375* (2013.01); *A61B 2018/00577* (2013.01); *A61B 2018/00642* (2013.01); *A61B 2018/00702* (2013.01); *A61B 2018/00791* (2013.01); *A61B 2018/00821* (2013.01); *A61B 2018/00839* (2013.01); *A61B 2018/00892* (2013.01); *A61B 2018/1405* (2013.01); *A61B 2018/1465* (2013.01); *A61B 2018/1497* (2013.01); *A61B 2218/002* (2013.01); *A61B 2562/125* (2013.01)

(56) References Cited

U.S. PATENT DOCUMENTS

| | | | |
|---|---|---|---|
| 4,805,621 A | 2/1989 | Heinze et al. | |
| 5,178,957 A | 1/1993 | Kolpe et al. | |
| 5,584,830 A | 12/1996 | Ladd et al. | |
| 5,702,386 A | 12/1997 | Stern et al. | |
| 5,797,903 A * | 8/1998 | Swanson .............. | A61L 29/085 600/374 |
| 5,971,983 A | 10/1999 | Lesh | |
| 6,012,457 A | 1/2000 | Lesh | |
| 6,024,740 A | 2/2000 | Lesh et al. | |
| 6,042,580 A | 3/2000 | Simpson | |
| 6,123,718 A | 9/2000 | Tu et al. | |
| 6,164,283 A | 12/2000 | Lesh | |
| 6,176,832 B1 | 1/2001 | Habu et al. | |
| 6,226,542 B1 | 5/2001 | Reisfeld | |
| 6,301,496 B1 | 10/2001 | Reisfeld | |
| 6,471,693 B1 | 10/2002 | Carroll et al. | |
| 6,522,930 B1 * | 2/2003 | Schaer .............. | A61B 18/1492 606/41 |
| 6,814,733 B2 | 11/2004 | Schwartz et al. | |
| 6,892,091 B1 | 5/2005 | Ben-Haim et al. | |
| 6,986,744 B1 | 1/2006 | Krivitski | |
| 6,997,924 B2 | 2/2006 | Schwartz et al. | |
| 7,156,816 B2 | 1/2007 | Schwartz et al. | |
| 7,340,307 B2 | 3/2008 | Maguire et al. | |
| 7,442,190 B2 | 10/2008 | Abbound et al. | |
| 7,536,218 B2 | 5/2009 | Govari et al. | |
| 7,756,576 B2 | 7/2010 | Levin | |
| 7,842,031 B2 | 11/2010 | Abboud et al. | |
| 8,357,152 B2 | 1/2013 | Govari et al. | |
| 9,126,023 B1 | 9/2015 | Sahatjian et al. | |
| 9,289,141 B2 | 3/2016 | Lowery et al. | |
| 2001/0031961 A1 | 10/2001 | Hooven | |
| 2002/0002369 A1 | 1/2002 | Hood | |
| 2002/0077627 A1 | 6/2002 | Johnson et al. | |
| 2003/0050637 A1 | 3/2003 | Maguire et al. | |
| 2003/0060820 A1 | 3/2003 | Maguire et al. | |
| 2005/0070887 A1 | 3/2005 | Taimisto et al. | |
| 2006/0013595 A1 | 1/2006 | Trezza et al. | |
| 2006/0135953 A1 | 6/2006 | Kania et al. | |
| 2007/0071792 A1 | 3/2007 | Varner et al. | |
| 2007/0287994 A1 | 12/2007 | Patel | |
| 2008/0018891 A1 | 1/2008 | Hell et al. | |
| 2008/0188912 A1 | 8/2008 | Stone et al. | |
| 2008/0249463 A1 | 10/2008 | Pappone et al. | |
| 2009/0182318 A1 | 7/2009 | Abboud et al. | |
| 2010/0324552 A1 | 12/2010 | Kauphusman et al. | |
| 2011/0130648 A1 | 6/2011 | Beeckler et al. | |
| 2011/0295248 A1 | 12/2011 | Wallace et al. | |
| 2012/0019107 A1 | 1/2012 | Gabl et al. | |
| 2012/0029511 A1 | 2/2012 | Smith et al. | |
| 2012/0071870 A1 | 3/2012 | Salahieh et al. | |
| 2012/0101413 A1 | 4/2012 | Beetel et al. | |
| 2012/0143177 A1 | 6/2012 | Avitall | |
| 2012/0191079 A1 | 7/2012 | Moll et al. | |
| 2013/0109982 A1 | 5/2013 | Sato et al. | |
| 2013/0165916 A1 * | 6/2013 | Mathur .................. | A61B 18/18 606/33 |
| 2013/0165941 A1 | 6/2013 | Murphy | |
| 2013/0261692 A1 | 10/2013 | Cardinal et al. | |
| 2013/0282084 A1 | 10/2013 | Mathur et al. | |
| 2014/0018788 A1 | 1/2014 | Engelman et al. | |
| 2014/0058197 A1 | 2/2014 | Salahieh et al. | |
| 2014/0121470 A1 | 5/2014 | Scharf et al. | |
| 2014/0148805 A1 | 5/2014 | Stewart et al. | |
| 2014/0243821 A1 * | 8/2014 | Salahieh .................. | A61N 1/05 606/41 |
| 2014/0276756 A1 | 9/2014 | Hill | |
| 2014/0276811 A1 | 9/2014 | Koblish et al. | |
| 2014/0288546 A1 | 9/2014 | Sherman et al. | |
| 2014/0357956 A1 | 12/2014 | Salahieh et al. | |
| 2015/0025532 A1 * | 1/2015 | Hanson .............. | A61B 18/1492 606/41 |
| 2015/0157382 A1 | 6/2015 | Avitall et al. | |
| 2016/0175041 A1 | 6/2016 | Govari | |
| 2016/0183877 A1 | 6/2016 | Williams et al. | |
| 2017/0042614 A1 | 2/2017 | Salahieh et al. | |
| 2017/0311829 A1 | 11/2017 | Becckler et al. | |
| 2017/0311893 A1 | 11/2017 | Beeckler et al. | |
| 2017/0347896 A1 | 12/2017 | Keyes et al. | |
| 2018/0161093 A1 | 6/2018 | Basu et al. | |

FOREIGN PATENT DOCUMENTS

| | | | |
|---|---|---|---|
| EP | 0779059 A1 | 6/1997 | |
| JP | 11-076233 A | 3/1999 | |
| JP | 2005-052424 A | 3/2005 | |
| JP | 2012-024156 A | 2/2012 | |
| WO | 0056237 A2 | 9/2000 | |
| WO | 02/102231 A2 | 12/2002 | |
| WO | 2008049087 A2 | 4/2008 | |
| WO | WO-2011143468 A2 * | 11/2011 | ............... A61B 5/01 |
| WO | 2013049601 A2 | 4/2013 | |
| WO | 2013052919 A2 | 4/2013 | |
| WO | 2013154776 A2 | 10/2013 | |
| WO | 2015049784 A1 | 4/2015 | |
| WO | 2015200518 A1 | 12/2015 | |
| WO | 2016183337 A2 | 11/2016 | |

OTHER PUBLICATIONS

Extended European Search Report for Application No. 17168513.4 dated Sep. 18, 2017, 11 pages.
Extended European Search Report for Application No. EP17168393.1 dated Dec. 15, 2017, 12 pages.
Extended European Search Report for European Application No. 17201434.2, dated Feb. 1, 2018, 9 pages.
Extended European Search Report for European Application No. 15201723, dated May 11, 2016, 7 pages.
Extended European Search Report for European Application No. 17168518, dated Sep. 20, 2017, 9 pages.
Extended European Search Report for European Application No. 17173893, dated Nov. 6, 2017, 8 pages.
Extended European Search Report for European Application No. 17205876, dated Jun. 1, 2018, 13 pages.
Partial European Search Report for Application No. 17168393.1 dated Sep. 13, 2017, 13 pages.

(56) References Cited

OTHER PUBLICATIONS

Partial European Search Report for European Application No. 17205876, dated Feb. 22, 2018, 10 pages.
International Search Report and Written Opinion for Application No. PCT/IB2019/052313, dated Jul. 22, 2019, 08 pages.

* cited by examiner

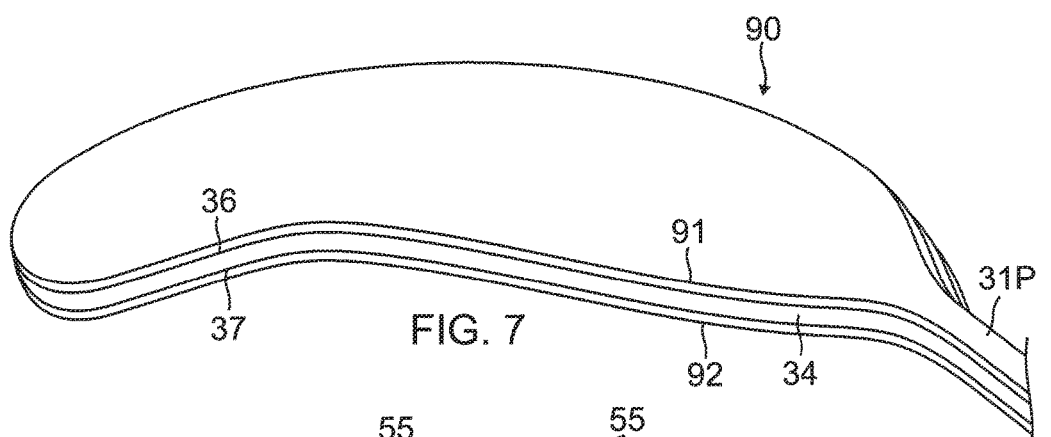
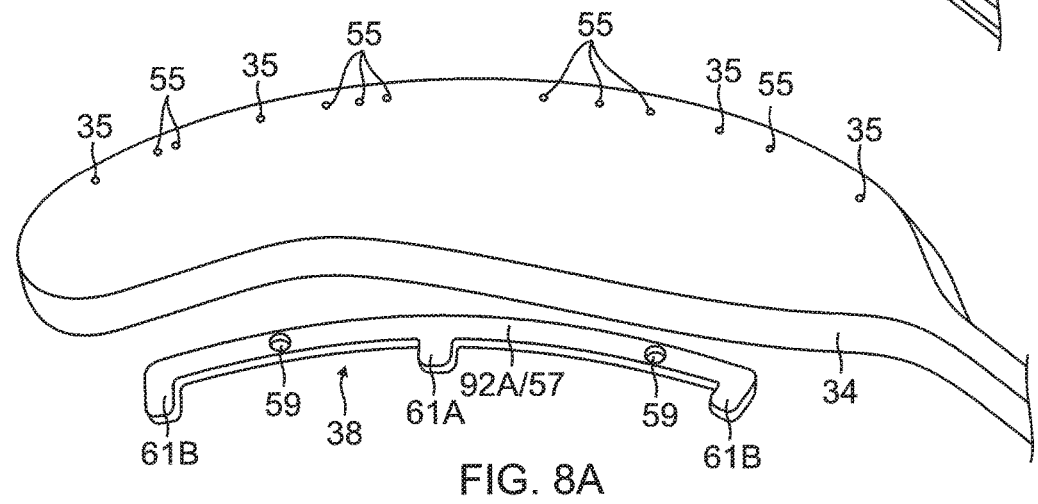
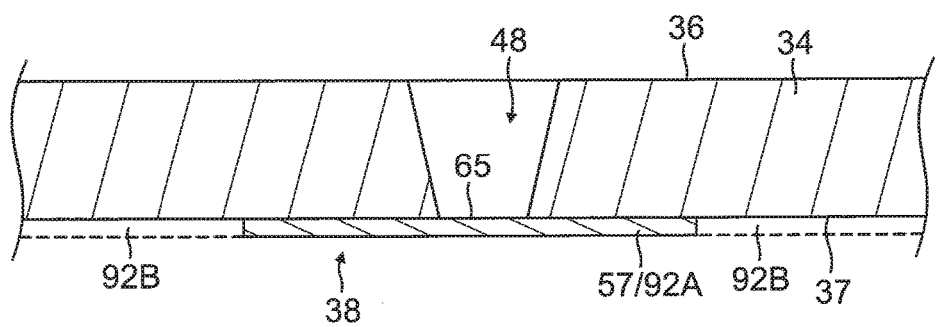

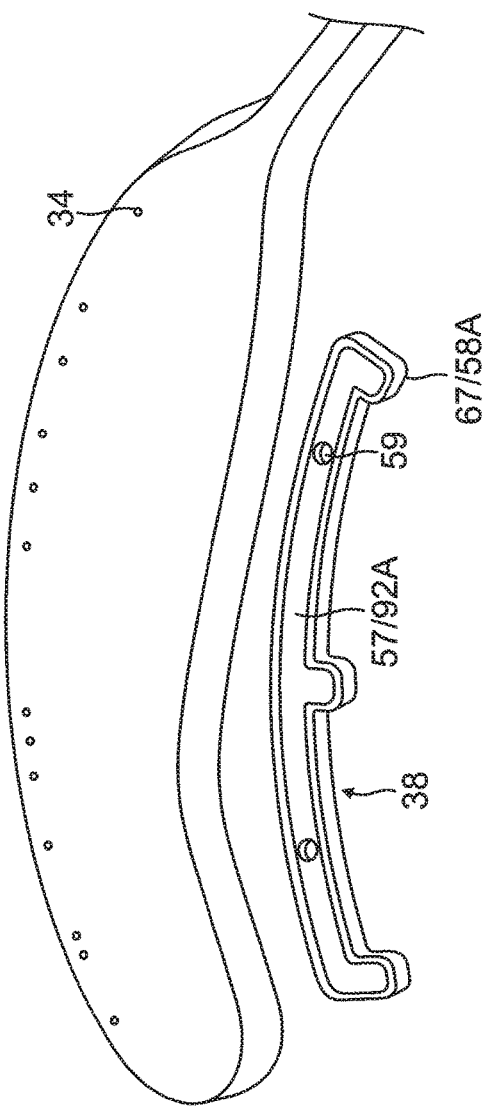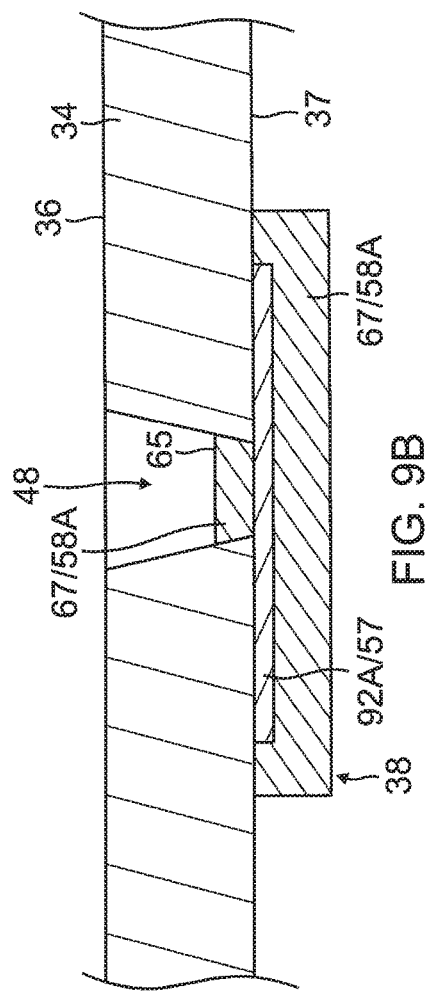

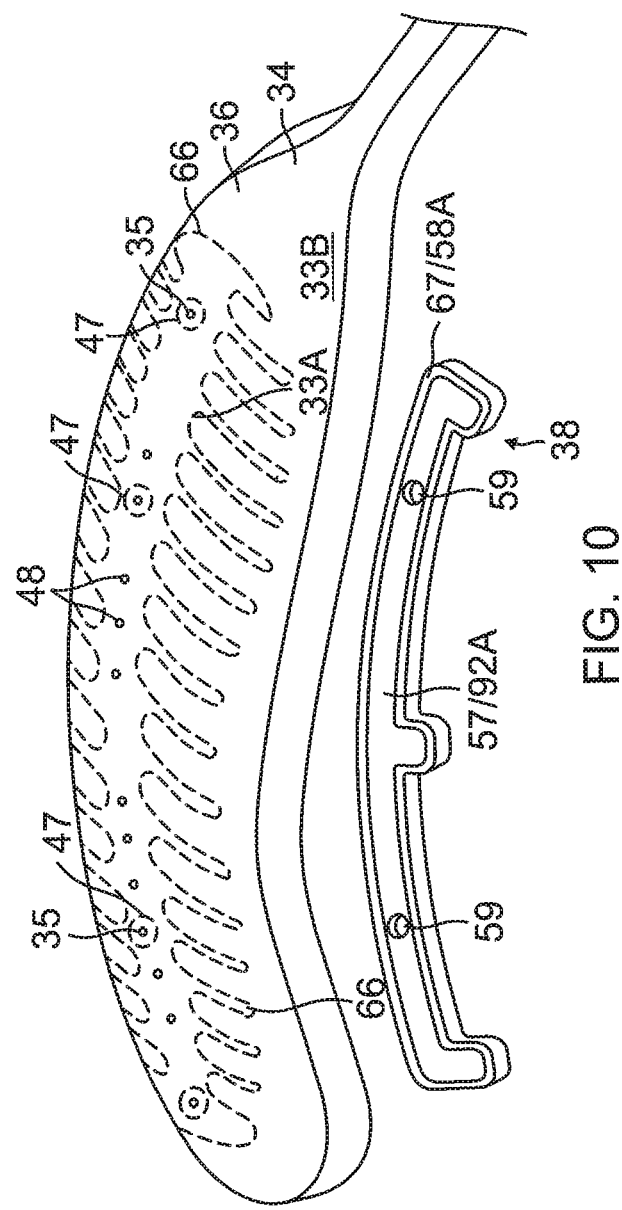

IRRIGATED BALLOON CATHETER WITH FLEXIBLE CIRCUIT ELECTRODE ASSEMBLY

CROSS REFERENCE TO RELATED APPLICATION(S)

This application is a continuation-in-part of and claims priority and the benefit of U.S. application Ser. No. 15/141,751, filed Apr. 28, 2016, titled METHOD OF CONSTRUCTING IRRIGATED BALLOON CATHETER, the entire content of which is incorporated herein by reference. This application is also a continuation-in-part of and claims priority and the benefit of U.S. application Ser. No. 15/172,118, filed Jun. 2, 2016, titled BALLOON CATHETER AND RELATED IMPEDANCE-BASED METHODS FOR DETECTING OCCLUSION, the entire content of which is incorporated herein by reference.

FIELD OF INVENTION

This invention relates to medical devices. More particularly, this invention relates to improvements in cardiac catheterization, including electrophysiologic (EP) catheters, in particular, EP catheters for mapping and/or ablating ostia and tubular regions in the heart.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

U.S. Pat. No. 6,814,733 to Schwartz et al., which is commonly assigned herewith and herein incorporated by reference, describes a catheter introduction apparatus having a radially expandable helical coil as a radiofrequency emitter. In one application the emitter is introduced percutaneously, and transseptally advanced to the ostium of a pulmonary vein. The emitter is radially expanded, which can be accomplished by inflating an anchoring balloon about which the emitter is wrapped, in order to cause the emitter to make circumferential contact with the inner wall of the pulmonary vein. The coil is energized by a radiofrequency generator, and a circumferential ablation lesion is produced in the myocardial sleeve of the pulmonary vein, which effectively blocks electrical propagation between the pulmonary vein and the left atrium.

Another example is found in U.S. Pat. No. 7,340,307 to Maguire, et al., which proposes a tissue ablation system and method that treats atrial arrhythmia by ablating a circumferential region of tissue at a location where a pulmonary vein extends from an atrium. The system includes a circumferential ablation member with an ablation element and includes a delivery assembly for delivering the ablation member to the location. The circumferential ablation member is generally adjustable between different configurations to allow both the delivery through a delivery sheath into the atrium and the ablative coupling between the ablation element and the circumferential region of tissue.

More recently, inflatable catheter electrode assemblies have been constructed with flex circuits to provide the outer surface of the inflatable electrode assemblies with a multitude of very small electrodes. Examples of catheter balloon structures are described in U.S. Publication No. 2016/0175041, titled Balloon for Ablation Around Pulmonary Vein, the entire content of which is incorporated herein by reference.

Flex circuits or flexible electronics involve a technology for assembling electronic circuits by mounting electronic devices on flexible plastic substrates, such as polyimide, Liquid Crystal Polymer (LCP), PEEK or transparent conductive polyester film (PET). Additionally, flex circuits can be screen printed silver circuits on polyester. Flexible printed circuits (FPC) are made with a photolithographic technology. An alternative way of making flexible foil circuits or flexible flat cables (FFCs) is laminating very thin (0.07 mm) copper strips in between two layers of PET. These PET layers, typically 0.05 mm thick, are coated with an adhesive which is thermosetting, and will be activated during the lamination process. Single-sided flexible circuits have a single conductor layer made of either a metal or conductive (metal filled) polymer on a flexible dielectric film. Component termination features are accessible only from one side. Holes may be formed in the base film to allow component leads to pass through for interconnection, normally by soldering.

However, due to variances in human anatomy, ostia and tubular regions in the heart come in all sizes. Thus, conventional balloon or inflatable catheters may not have necessary flexibility to accommodate different shapes and sizes while having sufficient structural support for effective circumferential contact with tissue. In particular, ablation electrodes that provide greater surface contact may lack sufficient flexibility. Moreover, delicate wires such as those of electrode lead wires and/or thermocouple wires and their solder joints need support and protection from breakage and damage during both assembly and use in the patient's body. Additionally, because the balloon configuration is radially symmetrical and multiple electrode elements surround the balloon configuration, determining the orientation of the balloon electrode assembly under fluoroscopy has also posed challenges.

Accordingly, there is a desire for a balloon or a catheter having an inflatable member with contact electrodes that can contact more tissue area while remaining sufficiently flexible to accommodate different anatomy and the tighter space constraints of an ostium and a pulmonary vein. There is also a desire for a balloon catheter to carry an electrode assembly with adaptations for the ostium and pulmonary vein that can be manufactured from a generic flexible circuit. There is a further desire for a balloon catheter capable of multiple functions including diagnostic and therapeutic functions, such as ablation, pacing, navigation, temperature sensing, electropotential sensing and impedance sensing, and be adaptive for use with other catheters, including a lasso catheter or a focal catheter.

SUMMARY OF THE INVENTION

The present invention is directed to a catheter having an irrigated inflatable balloon adapted for use in an ostium of a pulmonary vein. The balloon includes a flexible circuit electrode assembly adapted for circumferential contact with the ostium when the balloon is inflated. The balloon catheter is well suited for both diagnostic and therapeutic applications and procedures and may be used with a lasso catheter or focal catheter.

In some embodiments, an electrophysiology catheter adapted for use in an ostium, includes a balloon having an membrane, the balloon having a distal end and a proximal end defining a longitudinal axis; and a contact electrode supported on the membrane, the contact electrode configured for contact with the ostium, the contact electrode having a "fishbone" configuration with a longitudinally elongated portion and a plurality of transversal fingers.

In some more detailed embodiments, the transversal fingers have different lengths and the contact electrode has longer fingers and shorter fingers, the longer fingers being situated near an equatorial region of the balloon. Moreover, the plurality of fingers may include a distal finger, a proximal finger and fingers in between, wherein each of the fingers in between has a shorter adjacent finger. A width of the elongated portion may be greater than a width of each finger. The plurality of fingers may be generally evenly spaced along the elongated portion. The plurality of fingers may have a generally uniform width.

In some more detailed embodiments, the contact electrode comprises gold. The contact electrode may include a seed layer below the gold. A balloon may have a plurality of contact electrodes generally evenly radially distributed on its membrane.

In some embodiments, an electrophysiology catheter includes a balloon with a membrane, and a flex circuit electrode assembly on the membrane. The flex circuit has a substrate having a first surface and a second surface, a contact electrode on the first surface, a wiring electrode on the second surface, and a conductive via extending through the substrate and adapted to conductively connect the contact electrode and the wiring electrode.

In some more detailed embodiments, the substrate includes a first irrigation aperture, the membrane includes a second irrigation aperture aligned with the first irrigation aperture. Moreover, the contact electrode may include an exclusion zone surrounding the first irrigation aperture, and the wiring electrode may include an exclusion zone surrounding the first irrigation aperture. The wiring electrode may have an elongated body longitudinally aligned with the elongated portion. The wiring electrode may include a solder pad, wherein the flex circuit electrode assembly includes a wire pair conductively connected to the solder pad.

In additional more detailed embodiments, the flex circuit electrode includes a "fishbone" contact microelectrode, a "spine" wiring microelectrode, and a conductive via configured to conductively couple the contact microelectrode and the wiring electrode. The microelectrodes are strategically positioned relative to the electrodes to be close and proximate thereto but yet be physically and electrically isolated therefrom. The flex circuit electrode includes at least one exclusion zone configured to physically and electrically isolate the microelectrodes from the contact electrode and the wiring electrode. A microelectrode may be configured as an "island" surrounded circumferentially in its entirety by a contact electrode or a wiring electrode and physically and electrically isolated therefrom by an exclusion zone.

In some embodiments, the flex circuit electrode includes a proximal tail. Conductive wires configured for conductive connection to the contact electrode and/or the wiring electrode may extend between the proximal tail and the balloon membrane toward a shaft of the balloon catheter. In some embodiments, the conductive wires may extend through a through-hole formed in the balloon membrane to enter an interior of the balloon.

In some embodiments, the contact electrode and the wiring electrode may be split into a plurality of portions, with a respective contact electrode portion and a respective wiring electrode portion being conductively coupled by a conductive via. Conductive wires are provided for each conductively connected pair of contact electrode portion and wiring electrode portion. Each split electrode portion may surround a respective microelectrode physically and electrically isolated by an exclusion zone.

In some embodiments, conductive wires configured for conductive connection to the electrodes and the microelectrodes may be included in a ribbon cable. The ribbon cable may pass into an interior of the balloon through a through-hole formed in the balloon membrane. Alternatively, the ribbon cable may extend between a tail of the flex circuit electrode assembly and the balloon membrane toward proximal end of the balloon before entering a shaft proximal of the balloon.

In some embodiments, the flex circuit electrode assembly includes a thermocouple for use with a contact microelectrode, where the thermocouple has a wire pair which are embedded in the flex circuit substrate and connected to each other by a conducting via conductively coupled to the contact electrode. Advantageously, the thermocouple is configured to measure temperature of tissue in contact with the contact microelectrode while undergoing ablation by adjacent ablating contact electrode. Alternatively, when the tissue is not undergoing ablation, the thermocouple can concurrently sense electropotential signals from the tissue and the temperature of the tissue.

In some embodiments, the flex circuit electrode assembly includes a first and a second solder pads conductively coupled to first and second wires of the thermocouple, the solders pad being advantageously located remotely from the microelectrode, for example, in a region of the proximal tail, wherein a potential between the first and second solder pads comprises a signal representative of a temperature sensed by the thermocouple 400 at the location of the microelectrode 401. Moreover, each the solder pad, so electrically coupled, may also acquire electropotentials formed on its respective microelectrode 401 by its conductive via.

In some embodiments, solder pads coupled to a contact electrode, a microelectrode and a thermocouple for ablation, sensing electropotentials and temperature may be grouped as a set, where a flex circuit electrode assembly includes multiple sets of solder pads, all located remotely from the microelectrodes.

In some embodiments, the balloon catheter is configured for use with a second catheter, extending through a shaft of the balloon catheter. The second catheter may include a lasso catheter or a linear focal catheter.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIGS. 7, 8A, 9A, 10, 11A, 12A, 13A are exploded perspective views of a flexible circuit electrode assembly in different stages of construction, according to an embodiment of the present invention.

FIGS. 8B, 9B, 11B, 12B, 13B, 14 are side cross-sectional views of a flexible circuit electrode assembly in different stages of construction, according to an embodiment of the present invention.

DETAILED DESCRIPTION OF THE INVENTION

Overview

Figure 1:
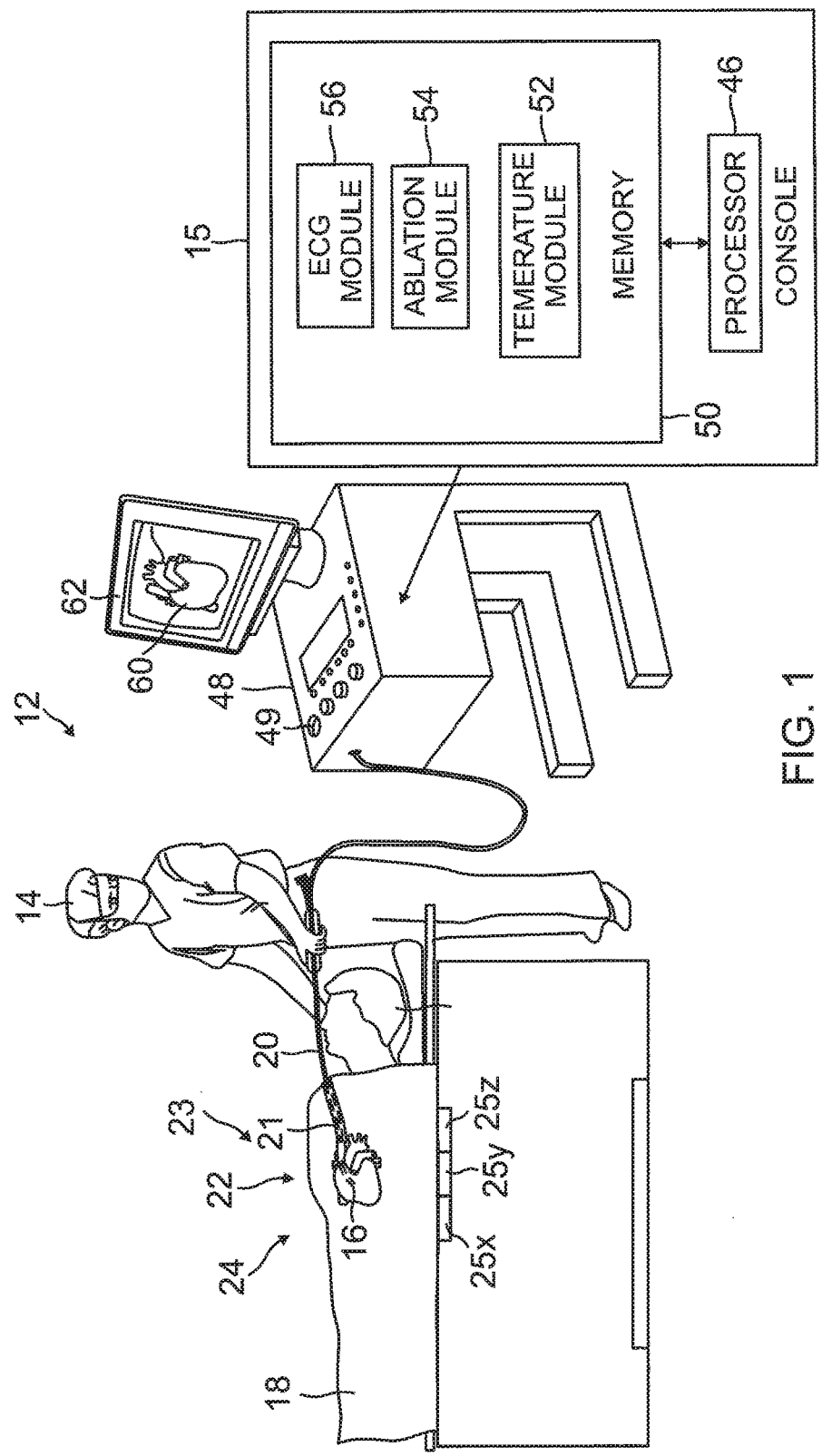
FIG. 1 is a schematic illustration of an invasive medical procedure, according to an embodiment of the present invention.

Ablation of cardiac tissue to correct a malfunctioning heart is a well-known procedure for implementing such a correction. Typically, in order to successfully ablate, cardia electropotentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation.

In contrast with prior art systems that use two or more separate instructions (e.g., one for the electropotential and temperature measurements, and another for the ablation), embodiments of the present invention facilitate the two measurements, and in addition enable ablation using radiofrequency electromagnetic energy, using a single balloon catheter. The catheter has a lumen, and an inflatable balloon is deployed through the catheter lumen (the balloon travels through the lumen in a collapsed, uninflated configuration, and the balloon is inflated on exiting the lumen). The balloon has an exterior wall or membrane and has a distal end and a proximal end which define a longitudinal axis that extends the lumen.

A multi-layer flexible metal structure is attached to an exterior wall or membrane of the balloon. The structure comprises a plurality of electrode groups arranged circumferentially about the longitudinal axis, where each electrode group comprises multiple ablation electrodes, typically arranged longitudinally.

Each electrode group may also include at least one micro-electrode that is insulated physically and electrically from the ablation electrodes in its group.

Each electrode group may also include at least a thermocouple.

In some embodiments, each electrode group has a microelectrode and a thermocouple formed at a common location.

Using a single balloon catheter, with the three functionalities of ability to perform ablation, electropotential measurement, and temperature measurement, simplifies cardiac ablation procedures.

System Description

In the following description, like elements in the drawings are identified by like numerals, and like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it is understood that embodiments of the present invention are not merely applicable to this specific procedure, and may include substantially any procedure on biological tissue or on non-biological materials.

Figure 2:
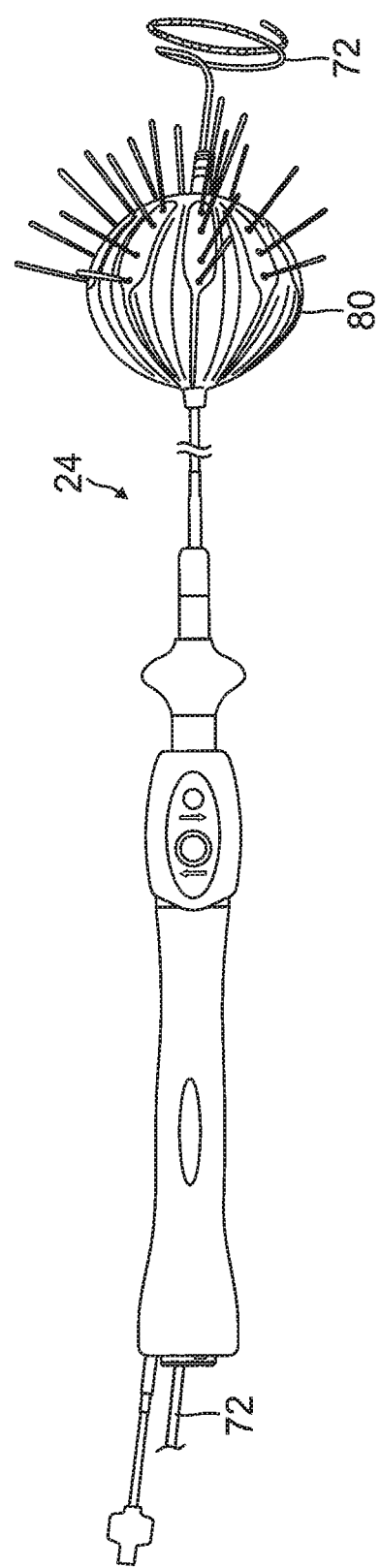
FIG. 2 is a top view of a balloon catheter of the present invention in its inflated state, in use with a lasso catheter, according to an embodiment of the present invention.

In order to perform the ablation, medical professional 14 inserts a probe 20 into a sheath 21 that has been pre-positioned in a lumen of the patient. Sheath 21 is positioned so that a distal end 22 of probe 20 enters the heart of the patient. A balloon catheter 24, which is described in more detail below with reference to FIG. 2, is deployed through a lumen 23 of the probe 20, and exits from a distal end of the probe 20.

As shown in FIG. 1, apparatus 12 is controlled by a system processor 46, which is located in an operating console 15 of the apparatus. Console 15 comprises controls 49 which are used by professional 14 to communicate with the processor. During the procedure, the processor 46 typically tracks a location and an orientation of the distal end 22 of the probe 20, using any method known in the art. For example, processor 46 may use a magnetic tracking method, wherein magnetic transmitters 25X, 25Y and 25Z external to the patient 18 generate signals in coils positioned in the distal end of the probe 20. The CARTO® available from Biosense Webster, Inc. of Diamond Bar, California, uses such a tracking method.

The software for the processor 46 may be downloaded to the processor in electronic form, over a network, for example. Alternatively or additionally, the software may be provided on non-transitory tangible media, such as optical, magnetic, or electronic storage media. The tracking of the distal end 22 is typically displayed on a three-dimensional representation 60 of the heart of the patient 18 on a screen 62.

In order to operate apparatus 12, the processor 46 communicates with a memory 50, which has a number of modules used by the processor to operate the apparatus. Thus, the memory 50 comprises a temperature module 52, an ablation module 54, and an electrocardiograph (ECG) module 56, the functions of which are described below. The memory 50 typically comprises other modules, such as a force module for measuring the force on the distal end 22, a tracking module for operating the tracking method used by the processor 46, and an irrigation module allowing the processor to control irrigation provided for the distal end 22. For simplicity, such other modules are not illustrated in FIG. 1. The modules may comprise hardware as well as software elements.

Figure 3:
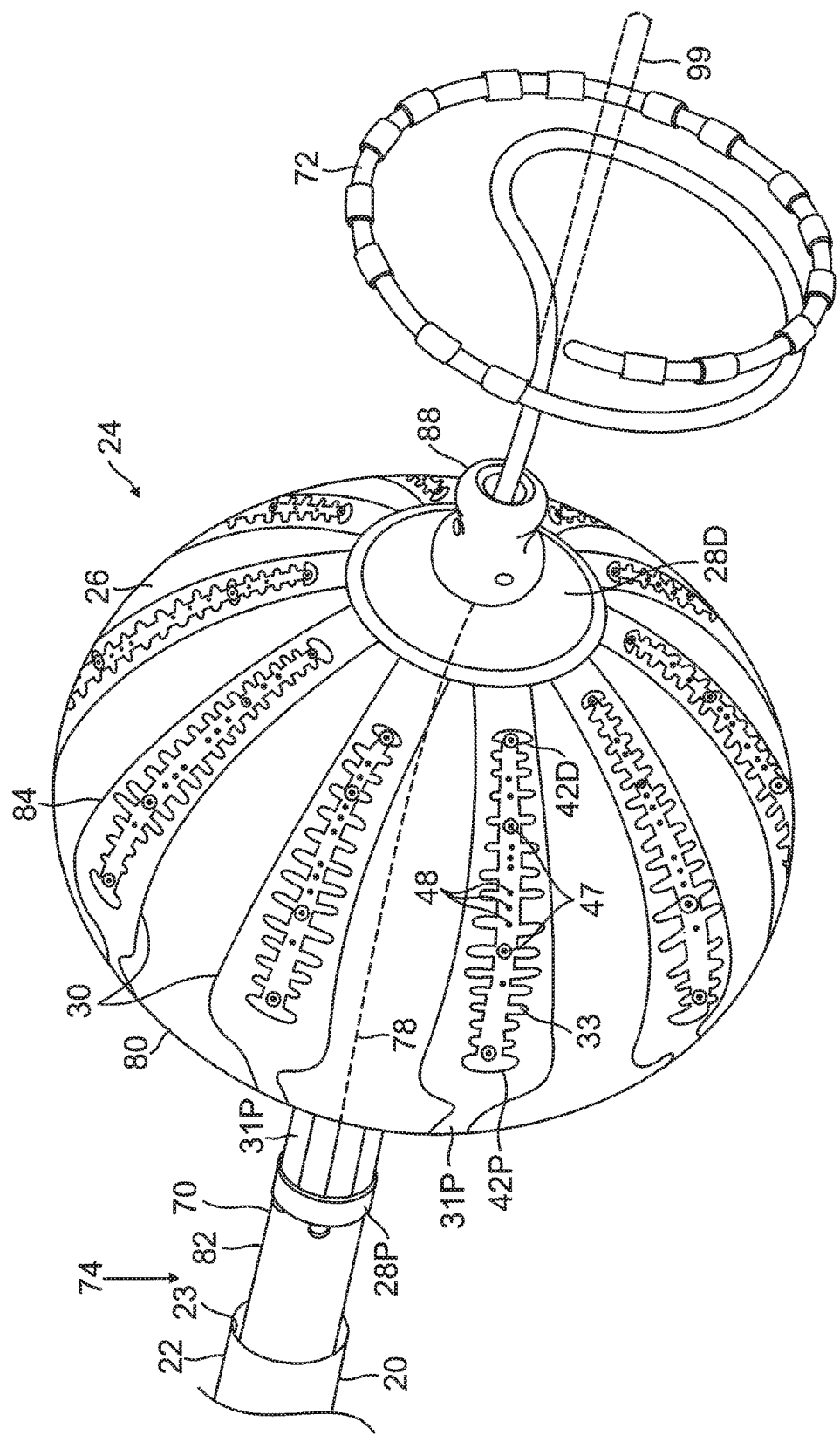
FIG. 3 is a perspective view of a balloon of the balloon catheter of FIG. 2, along with the lasso catheter.
Figure 4:
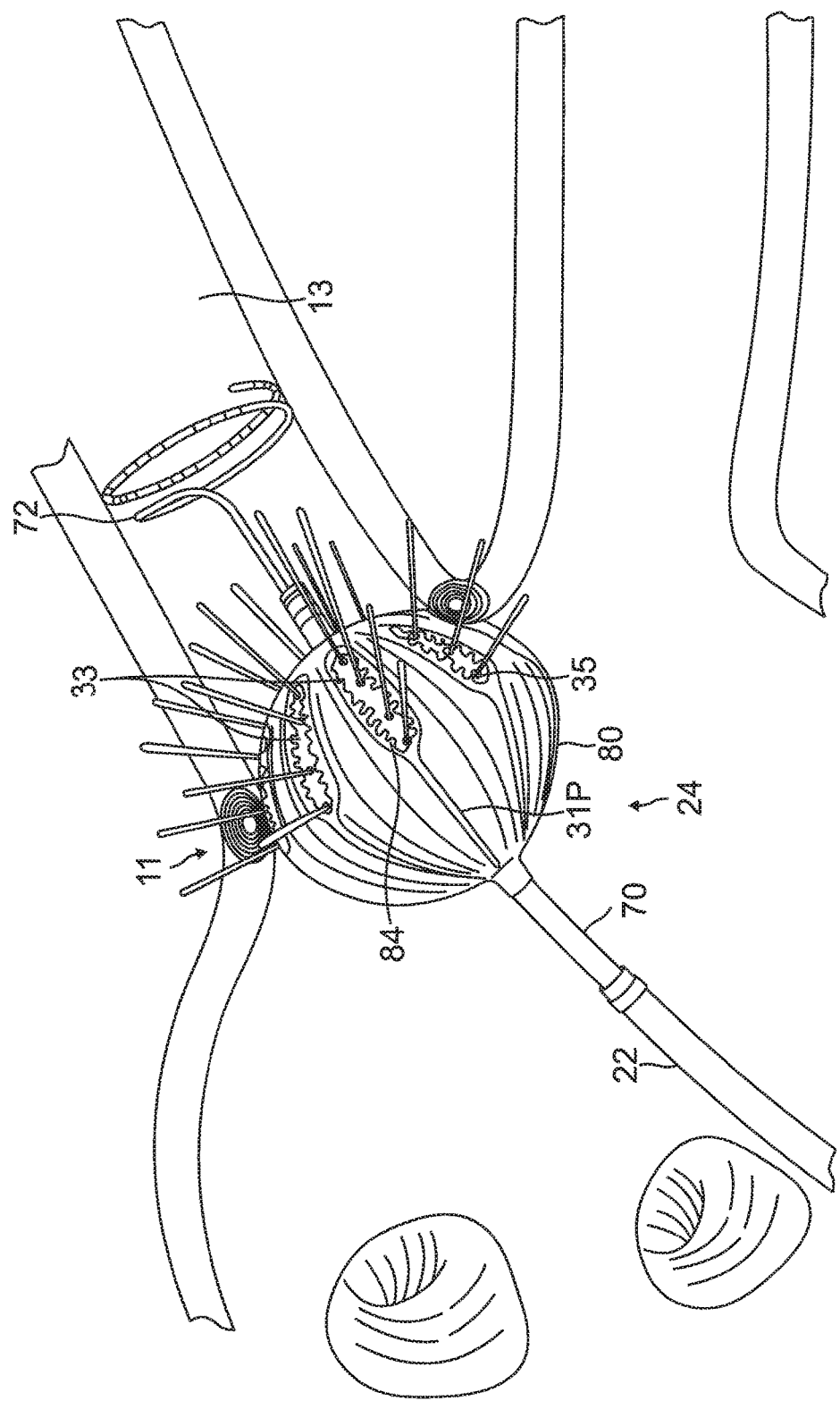
FIG. 4 is a side view of the balloon deployed in the region of a pulmonary vein and its ostium.

FIG. 3 is a schematic perspective view of the balloon catheter 24 in its inflated configuration, according to an embodiment of the present invention. In a disclosed embodiment, where the balloon catheter 24 is used to ablate an ostium 11 of a lumen, such as a pulmonary vein 13, as shown in FIG. 4, the balloon catheter 24 is supported by a tubular shaft 70 having a proximal shaft portion 82 and a distal shaft end 88. The shaft 70 comprises a hollow central tube 74, which permits a catheter to pass therethrough and past the distal shaft end 88. The catheter may be a focal linear catheter or a lasso catheter 72, as illustrated. The lasso catheter 72 may be inserted into the pulmonary vein to position the balloon catheter 24 correctly with respect to the ostium prior to ablation of the ostium. The distal lasso portion of the catheter 72 is typically formed of shape-memory retentive material such as nitinol. It is understood that the balloon catheter 24 may also be used with a linear or focal catheter 99 (as shown in broken lines in FIG. 3) in the PV or elsewhere in the heart. The focal catheter 99 may include a force sensor at its distal tip. Suitable force sending distal tips are disclosed in U.S. Pat. No. 8,357,152, issued on Jan. 22, 2013 to Govari et al., titled CATHETER WITH PRESSURE SENSING, and in U.S. Patent Application 2011/0130648, to Beeckler et al., filed Nov. 30, 2009, titled CATHETER WITH PRESSURE MEASURING TIP, the entire contents of both of which are incorporated herein by reference. Any catheter used in conjunction with the balloon catheter may have features and functions, including, for example, pressure sensing, ablation, diagnostic, e.g., navigation and pacing.

The inflatable balloon 80 of the balloon catheter 24 has an exterior wall or membrane 26 of a bio-compatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed uninflated configuration, via the lumen 23 of the probe 20, and may be inflated after existing from the distal end 22. The balloon 80 may be inflated and deflated by injection and expulsion of a fluid such as saline solution through the shaft 70. The membrane 26 of the balloon 80 is formed with irrigation pores or apertures 27 (shown in FIG. 6) through which the fluid can exit from the interior of the balloon 80 to outside the balloon for cooling the tissue ablation site at the ostium. While FIG. 2 and FIG. 4 show fluid exiting the balloon 80 as jet streams, it is understood that the fluid may exit the balloon with any desired flow rate and/or pressure, including a rate where the fluid is seeping out of the balloon.

Figure 5:
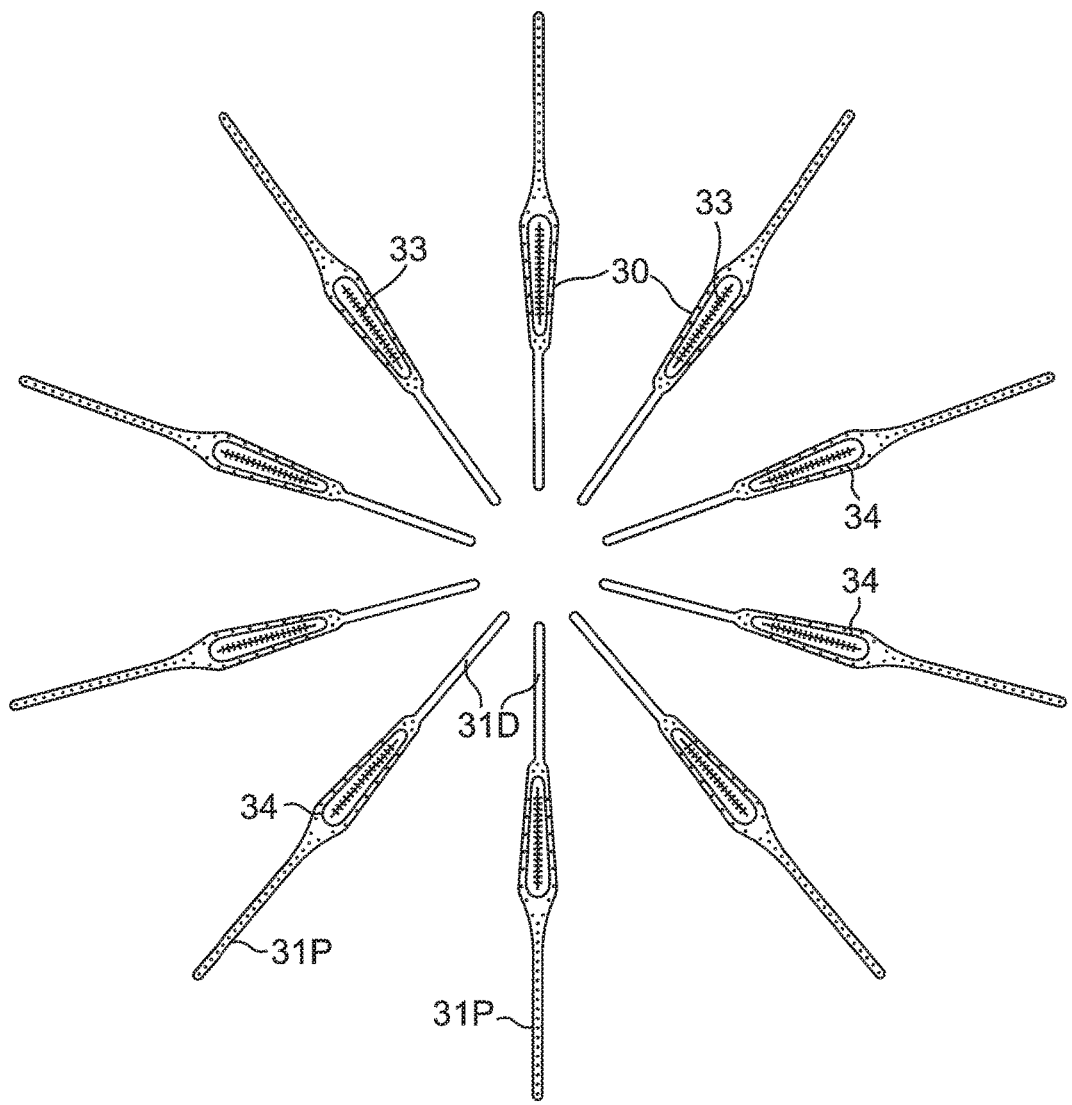
FIG. 5 is a top plan view of a plurality of flex circuit electrode assemblies, according to an embodiment of the present invention.

The membrane 26 supports and carries a combined electrode and temperature sensing member which is constructed as a multi-layer flexible circuit electrode assembly 84. The "flex circuit electrode assembly" 84 may have many different geometric configurations. In the illustrated embodiment, the flex circuit electrode assembly 84 has a plurality of radiating leaves or strips 30, as best seen in FIG. 5. The leaves 30 are evenly distributed about the distal end 88 and the balloon 80. Each leaf has wider proximal portion that gradually tapers to a narrower distal portion.

With reference to FIG. 3 and FIG. 5, each leaf 30 has a proximal tail 31P and a distal tail 31D. The proximal tail 31P is tucked under and fastened to the catheter 24 by a proximal ring 28P mounted on the proximal shaft portion 82 of the shaft 70. The distal tail 31D is tucked under and fastened to the catheter 24 by a distal ring (not shown). Either or both sets of tails 31D and 31P may be further covered by a respective semispherical cap, such as distal cap 28D. One or more contact electrodes 33 on each leaf come into galvanic contract with the ostium 11 during an ablation procedure, during which electrical current flows from the contact electrodes 33 to the ostium 11, as shown in FIG. 4.

Figure 6:
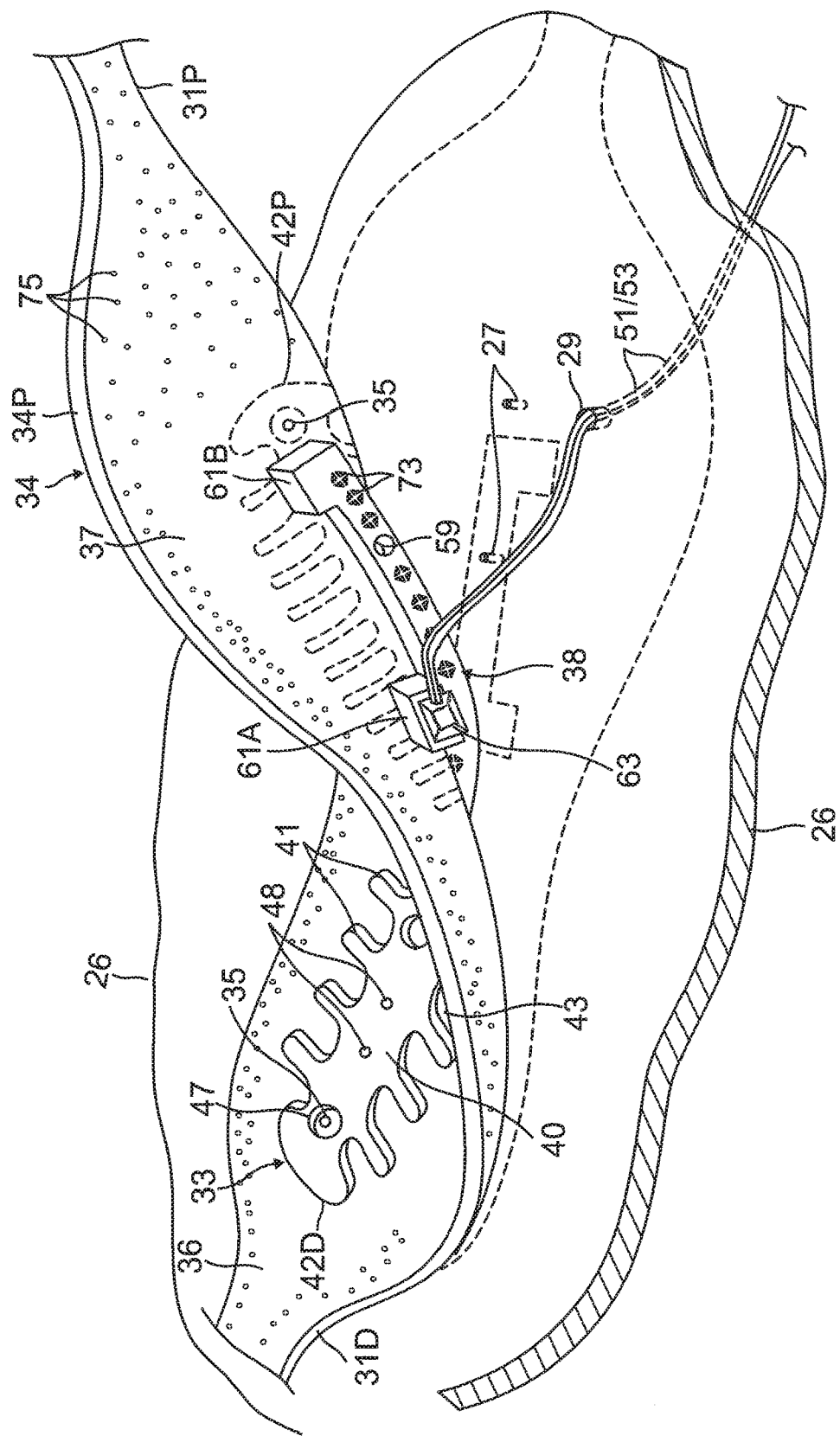
FIG. 6 is a perspective view of a flex circuit electrode assembly, accordingly to an embodiment of the present invention, partially lifted from the balloon.

For simplicity, the flex circuit electrode assembly 84 is described with respect to one of its leaf 30 as shown in FIG. 6, although it is understood that following description may apply to each leaf of the assembly. The flex circuit electrode assembly 84 includes a flexible and resilient sheet substrate 34, constructed of a suitable bio-compatible materials, for example, polyimide. In some embodiments, the sheet substrate 34 has a greater heat resistance (or a higher melting temperature) compared to that of the balloon membrane 26. In some embodiments, the substrate 34 is constructed of a thermoset material having a decomposition temperature that is higher than the melting temperature of the balloon membrane 26 by approximately 100 C or more.

The substrate 34 is formed with one or more irrigation pores or apertures 35 that are in alignment with the irrigation apertures 35 of the balloon member 26 so that fluid passing through the irrigation apertures 35 can pass to the ablation site on the ostium.

The substrate 34 has a first or outer surface 36 facing away from the balloon membrane 26, and a second or inner surface 37 facing the balloon membrane 26. On its outer surface 36, the substrate 34 supports and carries the contact electrodes 33 adapted for tissue contact with the ostium. On its inner surface 37, the substrate 34 supports and carries a wiring electrode 38. The contact electrode 33 delivers RF energy to the ostium during ablation and/or is connected to a thermocouple junction for temperature sensing of the ostium. In the illustrated embodiment, the contact electrode 33 has a longitudinally elongated portion 40 and a plurality of thin transversal linear portions or fingers 41 extending generally perpendicularly from each lateral side of the elongated portion 40 between enlarged proximal and distal ends 42P and 42D, generally evenly spaced therebetween. The elongated portion 40 has a greater width and each of the fingers has a generally uniform lesser width. Accordingly, the configuration or trace of the contact electrode 33 resembles a "fishbone." In contrast to an area or "patch" ablation electrode, the fingers 41 of the contact electrode 33 advantageously increase the circumferential or equatorial contact surface of the contact electrode 33 with the ostium while void regions 43 between adjacent fingers 41 advantageously allow the balloon 80 to collapse inwardly and/or expand radially as needed at locations along its equator. In the illustrated embodiment, the fingers 41 have different lengths, some being longer, others being shorter For example, the plurality of fingers include a distal finger, a proximal finger and fingers therebetween, where each of the fingers in between has a shorter adjacent finger. For example, each finger has a length different from its distal and/or proximal immediately adjacent neighboring finger(s) such that the length of each finger generally follows the tapered configuration of each leaf 30. In the illustrated embodiment, there are 22 fingers extending across (past each lateral side of) the elongated portion 40, with the longest finger being the third finger from the enlarged proximal end 42P. In some embodiments, the contact electrode 33 includes gold 58B with a seed layer 45, between the gold 58B and the membrane 26 (see FIG. 12A and FIG. 12B). The seed layer may include titanium, tungsten, palladium, silver, and/or combinations thereof.

Formed within the contact electrode 33 are one or more exclusion zone 47, each surrounding an irrigation aperture 27 formed in the substrate 26. The exclusion zones 47 are voids purposefully formed in the contact electrode 33, as explained in detail further below, so as to avoid damage to the contact electrode 33 during construction of the electrode assembly 84 in accommodating the irrigation apertures 27 at their locations and in their function.

Also formed in the contact electrode 33 are one or more conductive blind vias 48 which are conductive or metallic formations that extend through through-holes 55, as shown in FIG. 8A, in the substrate 34 and are configured as electrical conduits connecting the contact electrode 33 on the outer surface 36 and the wiring electrode 38 on the inner surface 37. It is understood that "conductive" is used herein interchangeably with "metallic" in all relevant instances.

In the illustrated embodiment, the contact electrode 33 measures longitudinally between about 0.1 inch and 1.0 inch, and preferably between about 0.5 inch and 0.7 inch, and more preferably about 0.57 inch, and has four exclusion zones 47 and nine blind vias 48.

On the inner surface 37 of the substrate 34, the wiring electrode 38 is generally configured as an elongated body generally similar in shape and size to the elongated portion 40 of the contact electrode 33. The wiring electrode 38 loosely resembles a "spine" and also functions as a spine in terms of providing a predetermined degree of longitudinal rigidity to each leaf 30 of the electrode assembly 84. The wiring electrode 38 is positioned such that each of the blind vias 48 is in conductive contact with both the contact electrode 33 and the wiring electrode 38. In the illustrated embodiment, the two electrodes 33 and 38 are in longitudinal alignment with other, with all nine blind vias 48 in conductive contact with both electrodes 33 and 38. In some embodiments, the wiring electrode 38 has an inner portion of copper 57 and an outer portion of gold 58.

The wiring electrode 38 is also formed with its exclusion zones 59 around the irrigation apertures 35 in the substrate 34. The wiring electrode 38 is further formed with solder pad portions 61, at least one active 61A, and there may be one or more inactive solder pad portions 61B. The solder pad portions 61A and 61B are extensions from a lateral side of the elongated body of the wiring electrode 38. In the illustrated embodiment, an active solder pad portion 61A is formed at about a mid-location along the elongated body, and a respective inactive solder pad portion 61B is provided at each of the enlarged distal end 42D and the enlarged proximal end 42P.

Attached, e.g., by a solder weld 63, to the active solder pad portion 61A are the wire pair, e.g., a constantan wire 51 and a copper wire 53. The copper wire 53 provides a lead wire to the wiring electrode 33, and the copper wire 53 and the constantan wire 51 provide a thermocouple whose junction is at solder weld 63. The wire pair 51/53 are passed through a through-hole 29 formed in the membrane 26. It is understood that, in other embodiments in the absence of the through-hole 29, the wire pair 51/53 may run between the membrane 26 and the substrate 34 and further proximally between the membrane 26 and the proximal tail 31P until the wire pair 51/53 enters the tubular shaft 70 via another through-hole (not shown) formed in the tubular shaft sidewall closer to the proximal ring 28.

Figure 14:
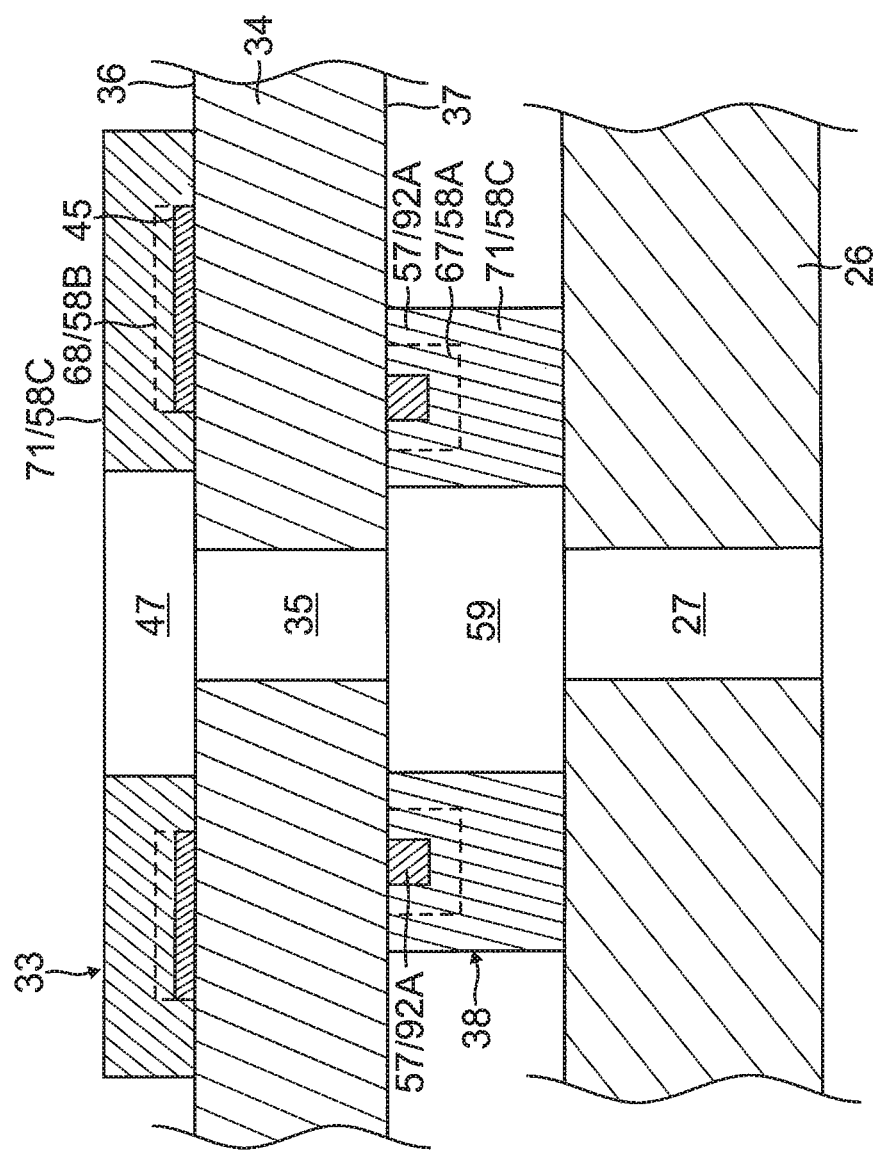

The flex circuit electrode assembly 84, including the leaves 30 and the tails 31P and 31D, is affixed to the balloon membrane 26 such that the outer surface 36 of the substrate 34 is exposed and the inner surface 37 of the substrate 34 is affixed to the balloon membrane 26, with the wiring electrode 38 and wire pair 51/53 sandwiched between the substrate 34 and the balloon membrane 26. The irrigation apertures 35 in the substrate 34 are aligned with the irrigation apertures 27 in the balloon membrane 26. The exclusion zones 59 in the wiring electrode 38 and the exclusion zones 47 in the contact electrode 33 are concentrically aligned with each other, as well as with the irrigation apertures 27 and 35, as shown in FIG. 14.

Methods of Construction

The present invention includes methods of constructing the flex circuit electrode assembly, and a balloon with the flex circuit electrode assembly. In some embodiments, the methods include the following Actions 1-9. It is understood that the Actions need not be taken in the sequence shown below, as desired or appropriate.

| Actions |
|---|
| 1 In forming a flex circuit electrode assembly, providing a flex circuit having a substrate, a first conductive layer and a second conductive layer. |
| 2 Removing the first conductive layer to expose a first surface of the substrate. |
| 3 Forming the wiring electrode in the second conductive layer; the forming may include forming an exclusion zone, active solder pad, and/or inactive solder pad. |
| 4 Forming through-holes in the substrate to provide one or more blind vias and one or more irrigation apertures. |
| 5 Applying a first added conductive layer on all exposed conductive surfaces. |
| 6 Forming the contact electrode on first surface of the substrate; the forming may include using a photoresist and application of a seed layer and a second added conductive layer; the forming may include forming one or more exclusion zones in |

| Actions |
|---|
| alignment with the irrigation apertures of the substrate. |
| 7 Applying another additional conductive layer on all exposed conductive surfaces on the substrate, the wiring electrode and the contact electrode to form a flex circuit electrode assembly. |
| 8 Preparing flex circuit electrode assembly for affixation; the preparing may include attaching wire pair to an active solder pad and/or perforating peripheral regions of substrate. |
| 9 Affixing the flex circuit electrode assembly to an outer surface of a balloon member. |

The Actions 1-9 are discussed in more detail below, with reference to FIGS. 7-13, in conjunction with FIG. 6.

1) Providing a flex circuit 90 having a flexible substrate 34 whose first or outer surface 36 is generally covered with a first conductive layer 91 and whose second or inner surface 37 is generally covered with a second conductive layer 92, as shown in FIG. 7. In some embodiments, the substrate 34 is constructed of polyimide and the first and second conductive layers 91 and 92 are copper.

2) Removing the first conductive layer 91, as shown in FIG. 8A and FIG. 8B. In some embodiment, the first conductive layer 91 of copper is removed from the outer surface 36 of the substrate 34 by chemical etching to expose the outer surface of the substrate.

3) Forming the wiring electrode 38 in the second conductive layer 92, as shown in FIGS. 8A and 8B. Forming the wiring electrode 38 may include forming the elongated body with at least an exclusion zone 59. Forming the wiring electrode 38 may include forming at least one active solder pad 61A. Forming the wiring electrode 38 may include forming at least one inactive solder pad 61B capable of functioning as a visual radiopaque marker. In some embodiments, forming the wiring electrode 38 includes masking a configuration of the elongated body in a first portion 92A of the second conductive layer 92, with one or more solder pads, while leaving unmasked a second portion 92B and one or more exclusion zones 59 in the first portion 92A; and removing the second conductive layer 92B in the unmasked one or more exclusion zones 59 and the second portion 92B from the inner surface 37 of the substrate 34 by chemical etching.

4) Forming one or more through-holes 55 in the substrate 34 to provide one or more blind vias 48 and forming one or more irrigation apertures 35, as shown in FIG. 8A and FIG. 9A. In some embodiments, forming a through-hole 55 and/or the irrigation aperture 35 includes laser drilling through the substrate 34 from a direction facing the outer surface 36, at location within a perimeter trace 66 (shown in broken lines in FIG. 10) of the contact electrode 33 and to a depth through the entire thickness of substrate 34. In forming the through-hole 55 for the blind via 48, the laser drilling is performed generally without penetrating the wiring electrode 38.

5) Applying an added conductive layer 67 on all exposed conductive surfaces on the substrate 34 and wiring electrode 38, as shown in FIG. 9A and FIG. 9B. In some embodiments, the substrate 34 with the wiring electrode 38 being formed is immersed in a gold plating bath to form a gold layer 58A covering exposed conductive surfaces of the elongated body of the wiring electrode 38 and a bottom surface 65 of any and all blind vias 48.

Figure 11A:
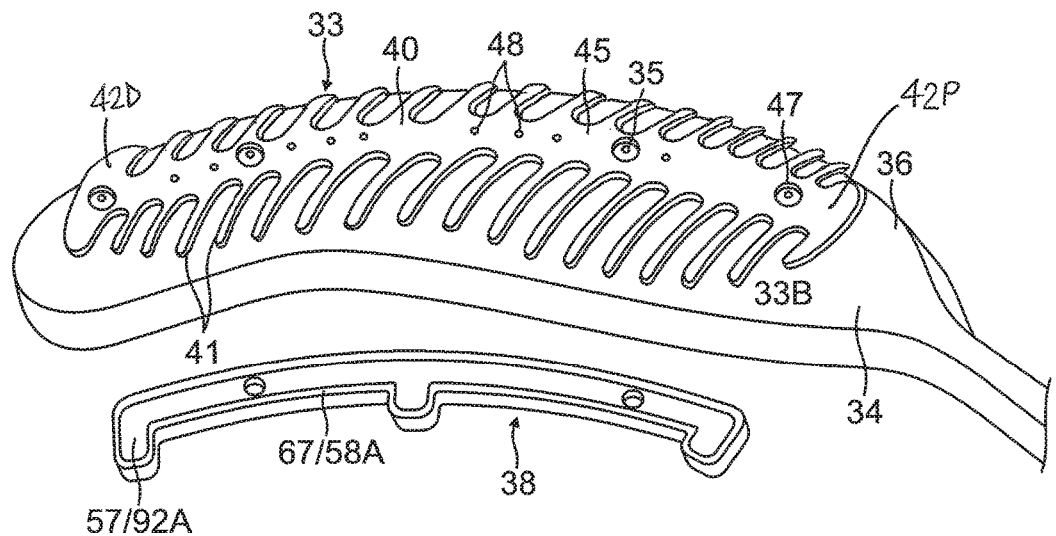
Figure 11B:
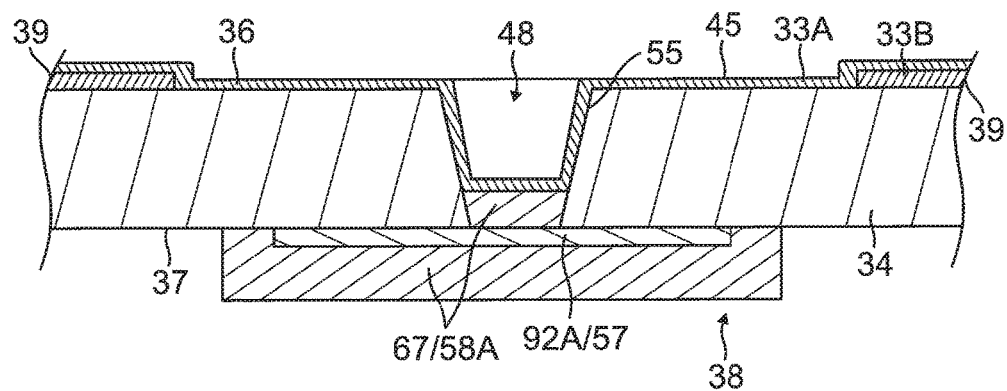
Figure 12A:
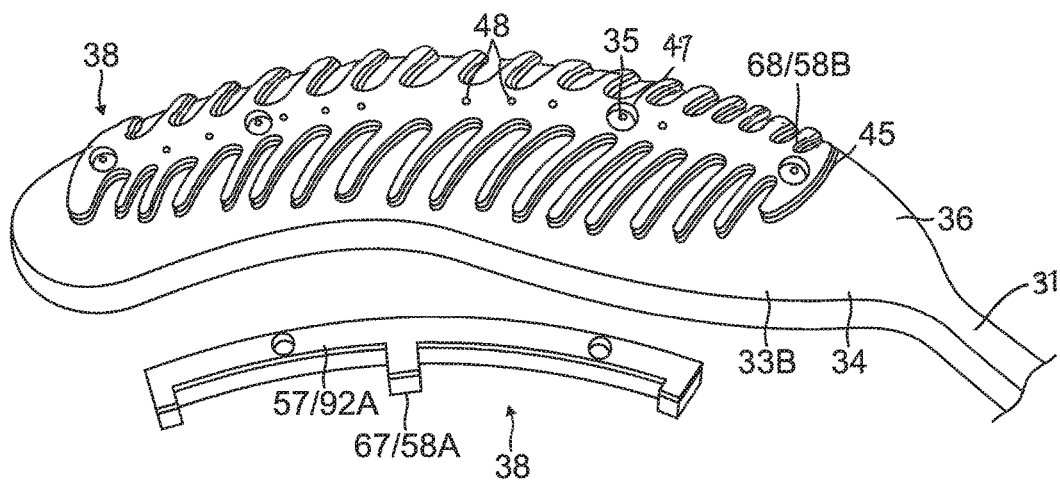
Figure 12B:
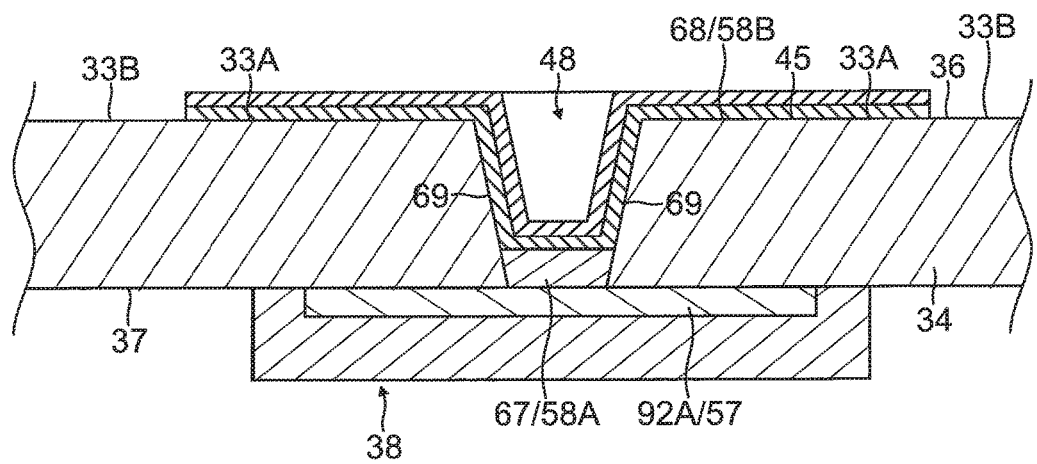

6) Forming the contact electrode 33 on the exposed outer layer 36 of the substrate 34, as shown in FIG. 10, FIG. 11A, FIG. 12A and FIG. 13. In some embodiments, forming the contact electrode 33 includes (i) defining a first region 33A within a perimeter trace 66 in a configuration of the fishbone (including the elongated body 40 and the fingers 41) on the outer surface 36 of the substrate 34, as shown in FIG. 10, (ii) applying photoresist 39 to a second region 33B outside of the first region 33A on the outer layer 36 of the substrate 34, as shown in FIG. 11B, (iii) applying a seed layer 45 onto the outer surface 36 of the substrate 34 in at least the first region 33A, as shown in FIG. 11A and FIG. 11B, (iv) applying another added conductive layer 68, e.g., gold 58B, on at least the seed layer 45, as shown in FIG. 12A and FIG. 12B, and (v) removing the photoresist 39 from the substrate 34 along with any portions of the seed layer 45 and the conductive layer 68 on the photoresist, as shown in FIG. 12A and FIG. 12B. In some embodiments, applying photoresist 39 includes applying photoresist 39 to one or more exclusion zones 47 in the elongated portion 40 of the contact electrode 33 surrounding an irrigation aperture 35 formed in the substrate 34. In some embodiments, applying a seed layer 45 includes sputtering the seed layer 45 to inside the one or more blind vias 48. In some embodiments, applying the conductive layer 68 includes sputtering the conductive layer 68 to inside the one or more blind vias 48. In some embodiments, the blind vias are formed with sloping or tapered sidewalls 69 (see FIG. 12B) which are covered with the seed layer 45 and the conductive layer 68/58B.

Figure 13A:
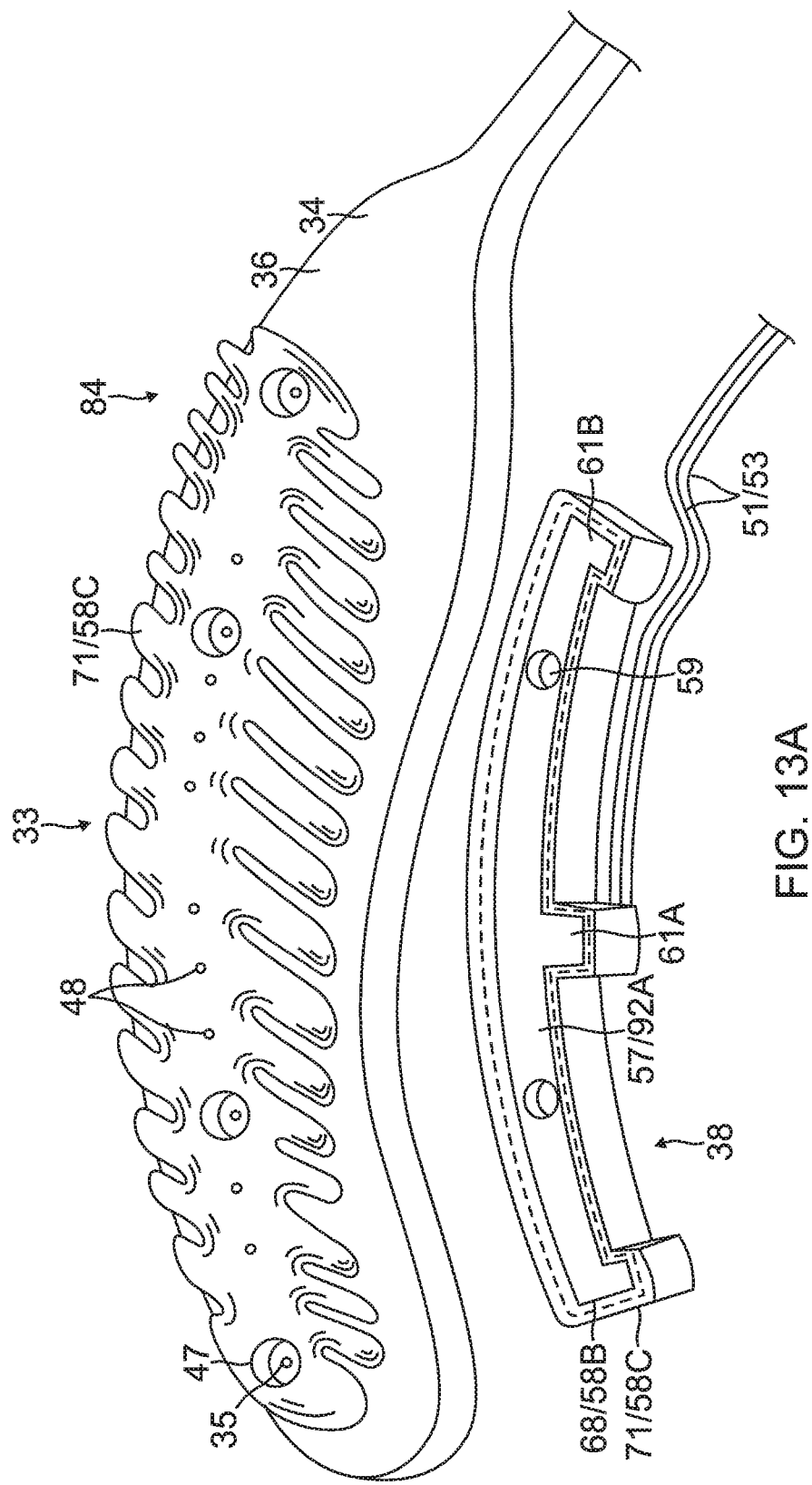
Figure 13B:
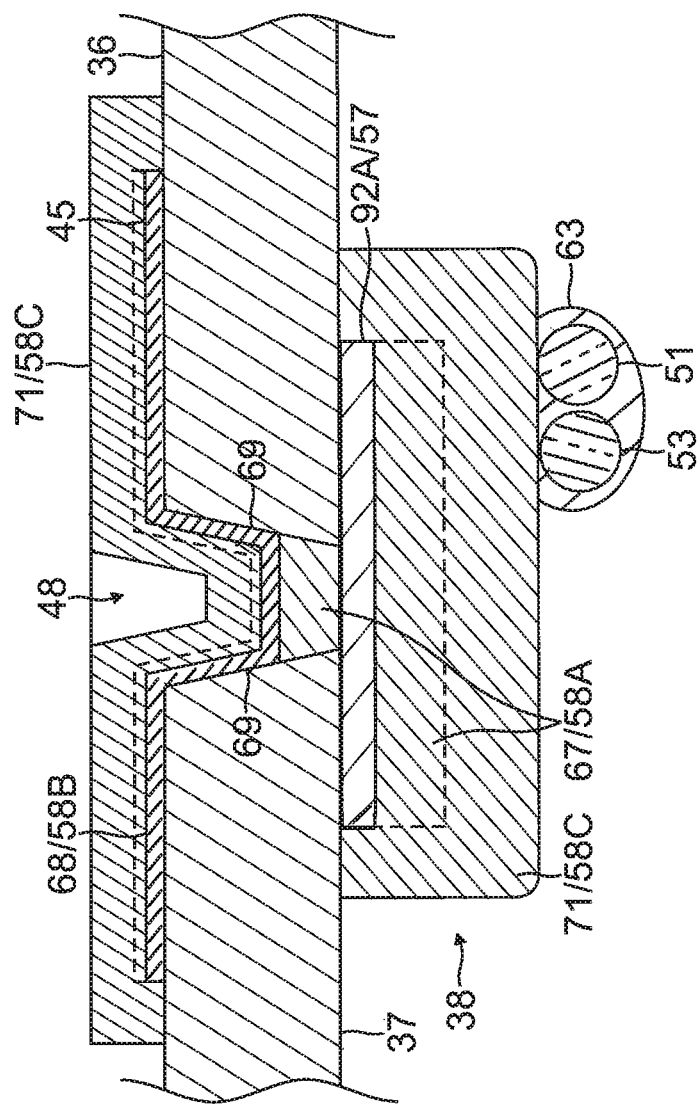

7) Applying yet another conductive layer 71 on all exposed conductive surfaces on the substrate 34, including the contact and wiring electrodes 33 and 38, as shown in FIG. 13A and FIG. 13B. In some embodiments, the substrate 34 inclusive of the electrodes 33 and 38 is immersed again in a gold plating bath to form another gold layer 58C covering exposed conductive surfaces of the electrode 33 and 38 and all blind vias 48. In some embodiments, radiopaque markers 73 are applied or painted onto the gold layer 58C covering the wiring electrode 38. For example, a mixture comprising tungsten and epoxy can be painted onto the gold layer 58C on the wiring electrode 38 to serve as radiopaque markers.

8) Preparing the flex circuit electrode assembly 84 for affixation to the balloon 80, as shown in FIG. 6. The Actions 1-7 described above form the electrodes 33 and 38 on the substrate 34 in forming a flex circuit electrode assembly 84 which may then be prepared for affixation to a balloon membrane 26. In some embodiments, the wire pair 51/53 are soldered to the active solder pad 61A, wherein the wire pair 51/53 function as a thermocouple, and the copper wire 53 functions as a lead wire delivering RF energy to the wiring electrode 38 which in turn energizes the contact electrode 33. In some embodiments, peripheral regions 34P of the substrate 34 are formed with a plurality of perforations 75 configured to receive an adhesive for affixing the electrode assembly 84 to the balloon membrane 26.

9) Affixing the flex circuit electrode assembly 84 to the balloon membrane 26, as shown FIG. 6. In some embodiments, the wire pair 51/53 are fed through a through-hole 29 formed in the membrane 26 of and an adhesive (not shown) is applied to generally the entire inner surface 37 of the substrate 34, inclusive of the wiring electrode 38, to adhere the flex circuit electrode assembly 84 to the membrane 26.

It is understood that the present invention includes other embodiments with more simplified actions and/or less actions than those described above. For example, forming the contact electrode in the configuration of a "fishbone" may include sputtering the seed layer and the second added conductive layer directly on the balloon membrane, thus eliminating the use of a substrate and a wiring electrode. Appropriate wiring may be provided in the configurations described herein and/or with similar blind vias, full vias (i.e., that pass through the contact electrode, the substrate, the wiring electrode, the contact microelectrode, and/or the wiring microelectrode), conductive traces, etc., as understood by one of ordinary skill in the art. Such a balloon catheter would nonetheless offer all the advantages afforded by a "fishbone" contact electrode, as described herein.

Figure 15A:
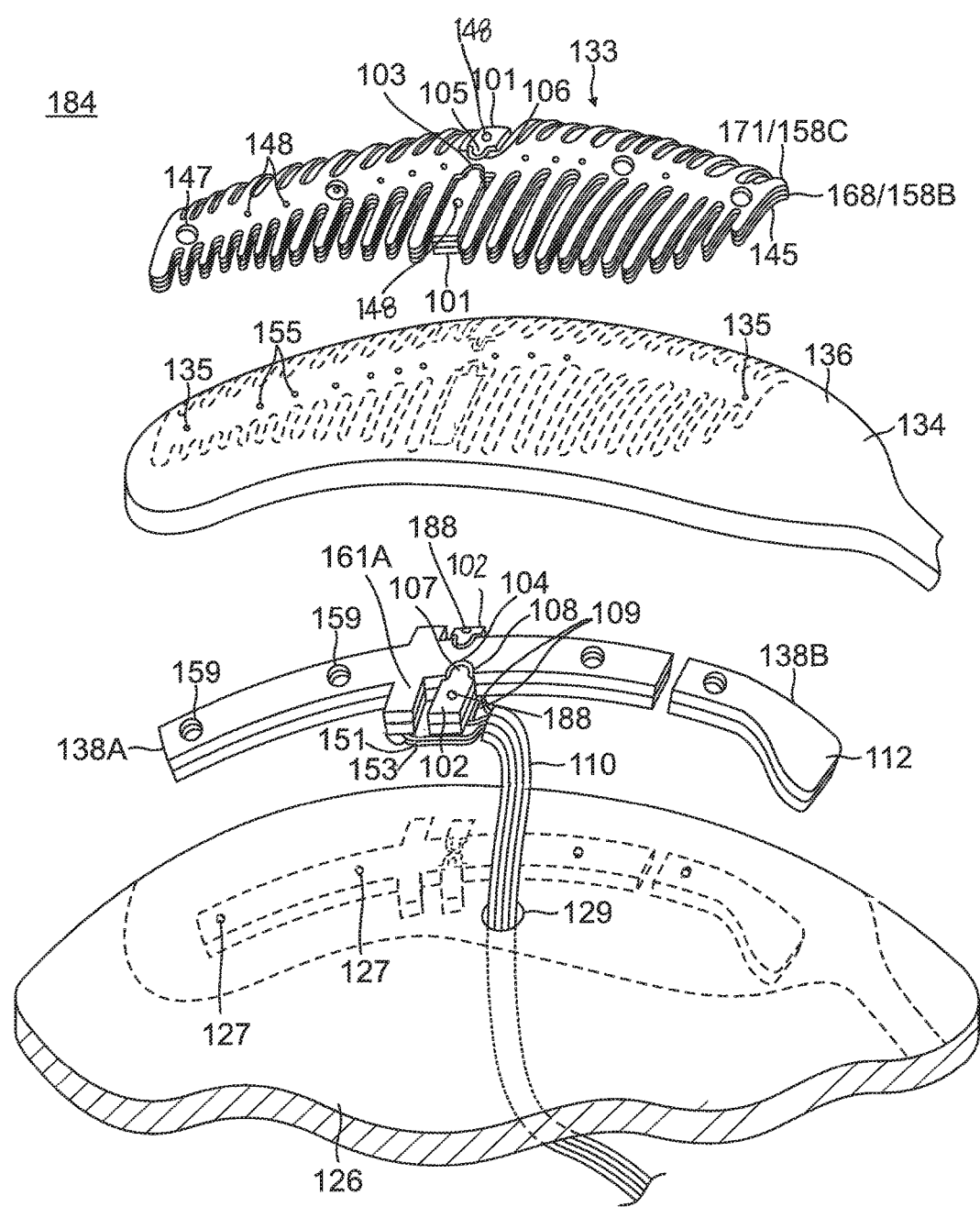
FIG. 15A is an exploded perspective view of a flexible circuit electrode assembly, according to another embodiment of the present invention, with parts of the contact electrode broken away to show its layers.

In other embodiments of the present invention, a flex circuit electrode assembly 184, as shown in FIG. 15A, includes one or more contact microelectrodes 101 and wiring microelectrodes 102 physically and electrically isolated from contact electrode 133 and wiring electrode 138, respectively. Pairs of aligned contact microelectrode 101 and wiring electrode 102 are conductively connected to each other by a blind via 148. The one or more microelectrodes 101 and 102 are formed concurrently with the formation of the respective electrode 133 and 138 per the aforementioned Actions. In the illustrated embodiment, the microelectrodes 101 and 102 are positioned near a midpoint along the length of the electrodes 133 and 138, so that the microelectrodes 101 and 102 are near the equatorial region of the balloon 80, although it is understood that they may be located at other locations relative to the electrodes 133 and 138. The microelectrodes 101 and 103 are configured for impedance, electrical signals, and/or temperature sensing independently of the electrodes 133 and 138 and thus are physically and electrically isolated from the contact electrode 133 and the wiring electrode 138, respectively by one or more respective exclusion zones 103 and 104.

Figure 15B:
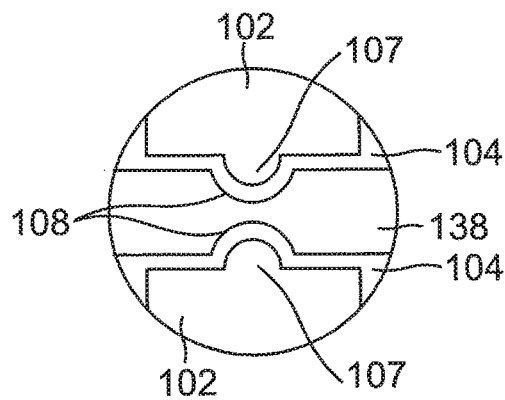
FIG. 15B is a detailed top plan view of a wiring microelectrode separated from a wiring electrode by an exclusion zone, according to an embodiment of the present invention.

For forming the wiring microelectrodes 102, for example, photoresist is applied to outer surface 136 of substrate 134 where the exclusion zones 103 are to be formed. In the illustrated embodiment, as shown in FIG. 15B, the wiring microelectrodes 102 are formed with protrusions 107 that project into conforming recesses 108 formed in elongated body of the wiring electrode 138. Spanning between the protrusions 107 and the recesses 108, the exclusion zones 104 adopt a conforming configuration between the wiring electrode 138 and the wiring microelectrode 102.

Figure 15C:
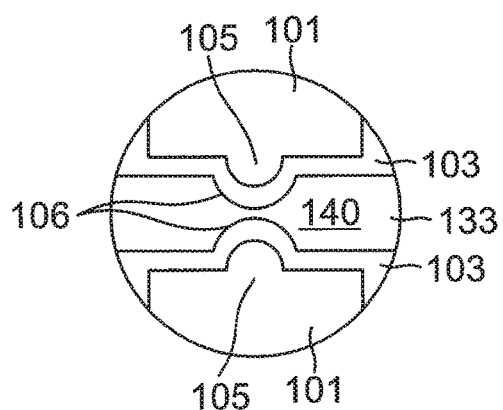
FIG. 15C is a detailed top plan view of a contact microelectrode separated from a contact electrode by an exclusion zone, according to an embodiment of the present invention.

For the contact microelectrodes 101, they are formed by appropriately masking a second conductive layer 192 (not shown) on inner surface 137 of the substrate 134 in the configuration of the contact microelectrodes 101. In the illustrated embodiment, as shown in FIG. 15C, the contact microelectrodes 101 are masked with protrusions 105 projecting into recesses 106 formed in elongated portion 140 of the contact electrode 133. Spanning between the protrusions 105 and the recesses 106, the exclusion zones 103 adopt a conforming configuration between the contact electrode 133 and the electrode 133 and the contact microelectrode 101.

The protrusions 105 and 107 allow the microelectrodes 101 and 102 to be as close as possible to the contact and wiring electrodes 133 and 138 and hence as close as possible to the tissue contact site, while maintaining physical and electrical isolation, Wire pair 151/153 are soldered to active solder pad 161A. A lead wire (e.g., copper wires) 109 is soldered to a respective wiring microelectrode 102. The wires 151, 153 and 109 are part of a ribbon cable 110 that extends through through-hole 129 formed in balloon membrane 126.

The wiring electrode 138 is shown as a "split" electrode comprising a first or distal elongated portion 138A and a second or proximal elongated portion 138B. The second wiring electrode portion 138B may function as a radiopaque marker with an enlarged portion 112 on one lateral side as a visual indicator under fluoroscopy of, for example, a specific wiring electrode, such as a "first" wiring electrode, and/or a direction toward subsequently numbered wiring electrodes around the circumference of balloon 180. The second wiring electrode portion 138B may also be active where respective lead wires are connected thereto to deliver RF energy to it. In the latter regard, however, it is understood that in some embodiments a plurality of active wiring electrodes (or active split wiring electrode portions) may each have its own copper wire while sharing a common constantan wire. In any instance, such wire pairs may provide both RF energizing functions and temperature sensing functions.

Figure 17:
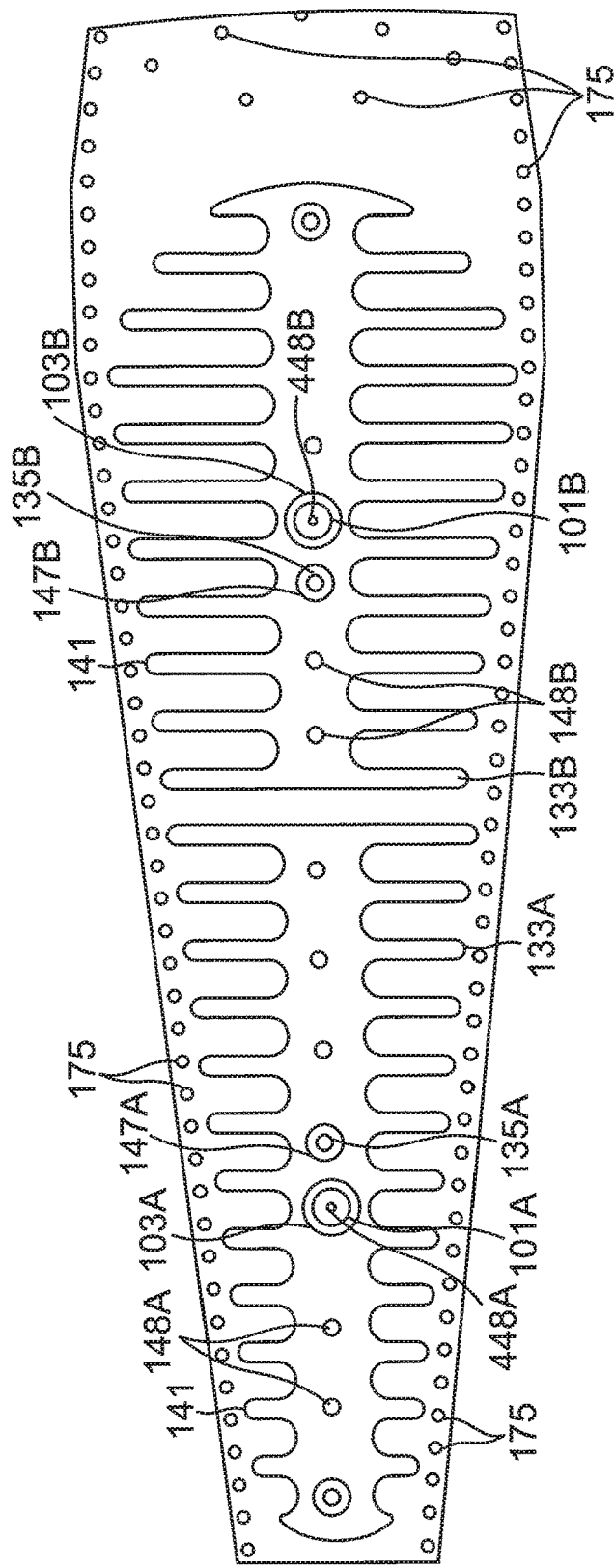
FIG. 17 is a top plan view of a flex circuit electrode assembly with a split contact electrode, according to an embodiment of the present invention.

As for the contact electrode 133, it may also be split into contact electrode portions 133A and 133B, as shown in FIG. 17, in correspondence with the split wiring electrode portions 138A and 138B, where the contact electrode portion 133A is conductively connected by blind vias 148A to the wiring electrode portion 138A, and contact electrode portion 133B is conductively connected by blind vias 148B to wiring electrode portion 138B.

Figure 16A:
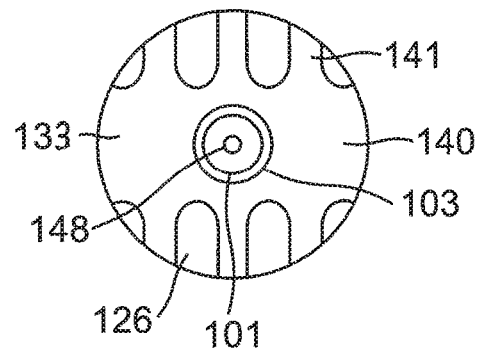
FIG. 16A is a detailed top plan view of an "island" contact microelectrode located in a contact electrode, according to an embodiment of the present invention.
Figure 16B:
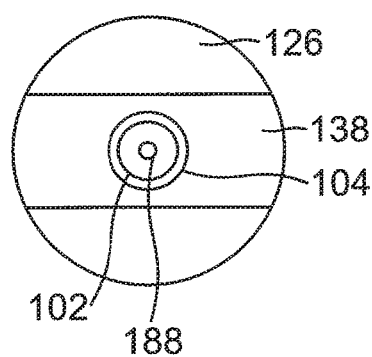
FIG. 16B is a detailed top plan view of an "island" contact microelectrode located in a contact electrode, according to an embodiment of the present invention.

It is understood that microelectrodes 101 and 102 may also be formed as "islands" (of any suitable shape and size), each surrounded in its entirety by the exclusion zones 106 and 107, respectively, formed in the electrodes 133 and 138 (in full, or in split electrode portions), respectively, as shown in FIG. 16A, FIG. 16B and FIG. 17. A blind via 148 may be formed in each contact microelectrode 101 to provide a conductive connection with its wiring microelectrode 102. A full via 188 may be formed in each wiring microelectrode 102 as a conductive connection to its wire pair, which can enable the microelectrodes 101 and 102 for ablation, electropotential, sensing, impedance detection and/or temperature sensing.

Figure 18A:
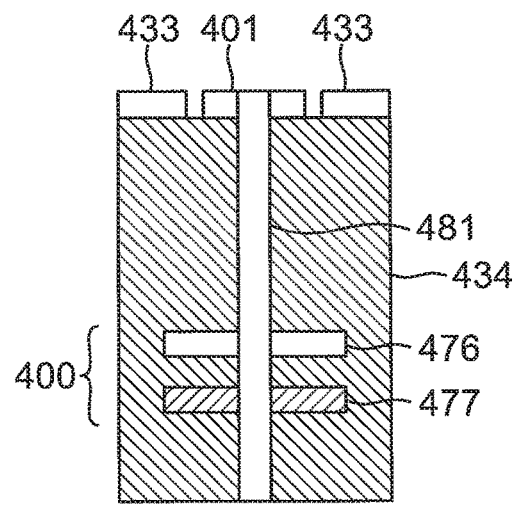
FIG. 18A is a side cross-sectional view of an embedded thermocouple, according to an embodiment of the present invention.

FIG. 18A illustrates a thermocouple 400 formed from a copper conductor or wire 476 connected to a constantan conductor or wire 477 by a conducting via 481. The wires 476 and 477 are formed as conducting lines embedded in substrate 424. The via 481 also connects to a contact microelectrode 401 on the outer surface of the substrate. By connecting the thermocouple 400 to the microelectrode 401, electropotential signals from tissue contacting the microelectrode 401 may be acquired while the temperature of the tissue is also measured. Alternatively, for instance in the case where contact electrode 433 is being used for ablation, the temperature of tissue contacting the microelectrode 401 may be measured without acquiring electropotential signals from the microelectrode 401.

Figure 18B:
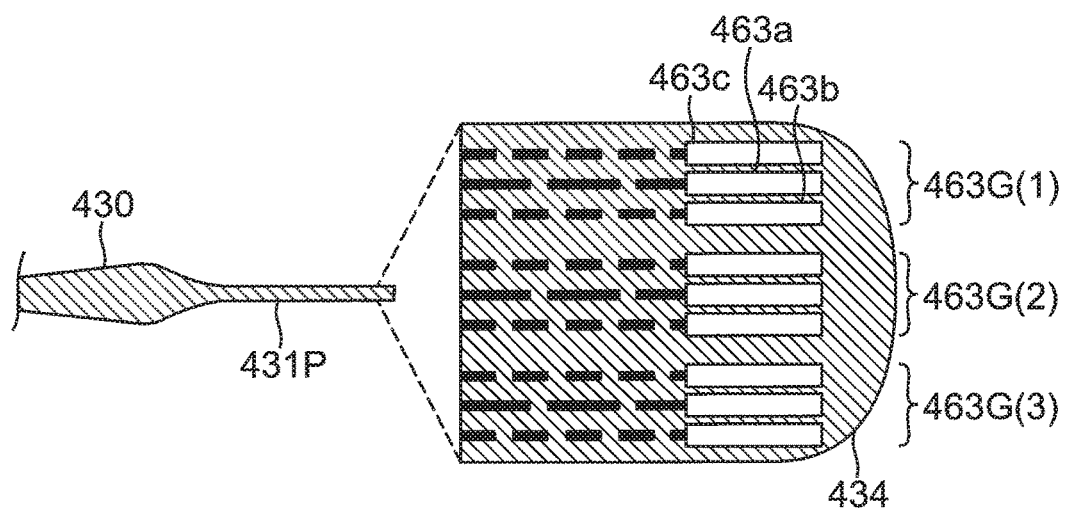
FIG. 18B is a top sectional view of an embedded solder pad sets, according to an embodiment of the present invention.

As shown in FIG. 18B, the wires 476 and 477 exit at solder pads 463a and 463b, respectively, which are located remotely from the microelectrode 401, in a region of the proximal tail 31P, for example, near its tip end. The potential between the solder pads 463a and 463b comprises a signal to the temperature module 52 in the console 15 (FIG. 1), and the module uses the signal to formulate the temperature measured by the thermocouple 400 at the location of the microelectrode 401. Moreover, the solder pad 463*a* connected to the copper wire 476 and/or the solder pad 463*b* connected to the constantan wire 477 may also be used to acquire electropotentials formed on the microelectrode 401 that the solder pad is connected to by via 481. The ECG module 56 of the console 15 (FIG. 1) typically receives signals derived from the solder pads 463*a* and/or 463*b*, and analyzes the signals to derive the electropotentials at the microelectrode 401.

A solder pad 463*c* is connected, via another conducting wire embedded in substrate 434, to contact electrode 433 and the solder pad 463*c* may be used to transfer electromagnetic RF ablation energy, generated by the ablation module 54 of the console 15 (FIG. 1), to the contact electrode 433. As shown in FIG. 18B, the solder pads 463*c*, 463*a* and 463*b* may be grouped as a set of three solder pads 463G(1) connecting to the contact electrode 433, the microelectrode 401 and the thermocouple 400. A set of three pads 463G(i) may be connected to a set of contact electrode, microelectrode and thermocouple. Notably, the location of at least the solder pads 463*a* and 463*b* can be advantageously remote from the location of where the temperature is measured, so that any bulkiness embodied in the solder pads 463*a* and 463*b* can be avoided at location of the microelectrode 401 where tissue contact occurs.

As shown in FIG. 15, irrigation apertures 127 are formed in the balloon membrane 126, irrigation apertures 135 are formed in the substrate 134, exclusion zones 147 are formed in the contact electrode 133, and exclusion zones 159 are formed in the wiring electrode 138.

In some embodiments, the substrate 34, 134 (e.g., polyimide) has a thickness of about 25.0 microns. The wiring electrode 38, 138 includes an inner layer of copper having a thickness of about 2.0 microns and an outer layer of gold of having a thickness of ranging between about 1.0 and 50 microns, and preferably between about 2.75 microns and 37 microns, where the thickness of the gold depends on how much radiopacity is desired or appropriate. The contact electrode 33, 133 includes a seed layer having a thickness of about 0.01-0.05 microns and an outer layer of gold having a thickness of about 1.0 micron. The balloon membrane 26, 126 may have an average thickness of about 25.0 microns as it understood that the membrane may have a nonuniform thickness due to the method of manufacture.

In operation, the wire pair 51/53 conduct RF energy provided by the ablation module 54 of the console 15 (FIG. 1) through the control handle and the catheter shaft to the wiring electrode 38 which in turn energizes the contact electrode 33 through the blind vias 48.

In some embodiments, where the balloon 80 includes a flex circuit electrode assembly with 10 leaves (providing 10 contact electrodes), 10 functionally satisfactory lesions can be generated by discharging 25 W of RF power through each of the contact electrode 33 simultaneously, i.e., for a total of 250 W, for ten seconds or less. By generating lesions using high power in short durations, effectively using a "pulse" of power, heat dissipation from the site being ablated is minimized. In other words, the short duration of ablation helps to concentrate the heat energy at the site, and less energy is transferred away from the site.

In other embodiments, suitable ranges of power supplied to each contact electrode include between about 15-25 W for 10 seconds and 10-20 W for 60 seconds. In other embodiments, the power supplied to each contact electrode is at 25 W or higher for ten seconds or less.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter adapted for use in an ostium, comprising:
    a balloon having an membrane, the balloon having a distal end and a proximal end defining a longitudinal axis; and
    a contact electrode supported on the membrane, the contact electrode configured for contact with the ostium, the contact electrode having a fishbone configuration with a longitudinally elongated portion and a plurality of transversal fingers,
    wherein at least two of the transversal fingers have different lengths.

2. An electrophysiology catheter of claim 1, wherein the contact electrode comprises gold.

3. An electrophysiology catheter of claim 2, wherein the contact electrode comprises a seed layer below the gold.

4. An electrophysiology catheter of claim 1, wherein the contact electrode has longer fingers and shorter fingers, the longer fingers being situated near an equatorial region of the balloon.

5. An electrophysiology catheter of claim 1, wherein the plurality of fingers include a distal finger, a proximal finger and fingers in between, wherein each of the fingers in between has a shorter adjacent finger.

6. An electrophysiology catheter of claim 1, wherein a width of the elongated portion is greater than a width of each finger.

7. An electrophysiology catheter of claim 1, wherein the plurality of fingers are generally evenly spaced along the elongated portion.

8. An electrophysiology catheter of claim 1, wherein the plurality of fingers have a generally uniform width.

9. An electrophysiology catheter of claim 1, further comprising a plurality of contact electrodes generally evenly radially distributed on the balloon membrane.

10. An electrophysiology catheter, comprising:
    a balloon with a membrane; and
    a flex circuit electrode assembly on the membrane, having:
        a substrate having a first surface and a second surface;
        a contact electrode on the first surface, wherein the contact electrode has an elongated portion and a plurality of transversal fingers, and wherein at least two of the transversal fingers have different lengths;
        a wiring electrode on the second surface; and
        a conductive via extending through the substrate and adapted to conductively connect the contact electrode and the wiring electrode.

11. The electrophysiology catheter of claim 10, wherein the substrate includes a first irrigation aperture, the membrane includes a second irrigation aperture aligned with the first irrigation aperture.

12. The electrophysiology catheter of claim 11, wherein the contact electrode includes an exclusion zone surrounding the first irrigation aperture.

13. The electrophysiology catheter of claim 11, wherein the wiring electrode includes an exclusion zone surrounding the first irrigation aperture.

14. The electrophysiology catheter of claim 10, wherein the wiring electrode includes a solder pad.

15. The electrophysiology catheter of claim 14, wherein the flex circuit electrode assembly includes a wire pair conductively connected to the solder pad.

16. The electrophysiology catheter of claim 10, wherein the flex circuit electrode assembly includes:
 a contact microelectrode;
 a wiring microelectrode; and
 a conductive via configured to conductively connect the contact microelectrode and the wiring electrode.

17. The electrophysiology catheter of claim 16, wherein the flex circuit electrode includes at least one exclusion zone configured to physically and electrically isolate the microelectrodes from the contact electrode and the wiring electrode.

18. The electrophysiology catheter of claim 10, wherein the wiring electrode has an elongated body longitudinally aligned with the elongated portion.

* * * * *